(12) United States Patent
Tsukagoshi et al.

(10) Patent No.: US 10,463,328 B2
(45) Date of Patent: Nov. 5, 2019

(54) MEDICAL IMAGE DIAGNOSTIC APPARATUS

(71) Applicant: Toshiba Medical Systems Corporation, Otawara-shi (JP)

(72) Inventors: Shinsuke Tsukagoshi, Nasushiobara (JP); Takahiro Goto, Utsunomiya (JP); Go Mukumoto, Obu (JP)

(73) Assignee: Canon Medical Systems Corporation, Otawara-shi (JP)

( * ) Notice: Subject to any disclaimer, the term of this patent is extended or adjusted under 35 U.S.C. 154(b) by 33 days.

(21) Appl. No.: 15/590,654

(22) Filed: May 9, 2017

(65) Prior Publication Data
US 2017/0319164 A1  Nov. 9, 2017

(30) Foreign Application Priority Data

May 9, 2016  (JP) .................................. 2016-094081
May 8, 2017  (JP) .................................. 2017-092526

(51) Int. Cl.
*A61B 6/00* (2006.01)
*G06T 7/73* (2017.01)
(Continued)

(52) U.S. Cl.
CPC ............ *A61B 6/469* (2013.01); *A61B 6/5205* (2013.01); *G06T 7/75* (2017.01); *A61B 6/027* (2013.01);
(Continued)

(58) Field of Classification Search
CPC ......... G06T 7/0012; G06T 2207/30008; G06T 2207/10072; G06T 2210/41; G06T 19/00;
G06T 2207/10081; G06T 7/75; G06T 2207/30101; G06T 17/00; G06T 2207/30048; G06T 2200/04; G06T 2207/10116; G06T 2207/30096; A61B 6/649; A61B 34/10; A61B 6/5217;
(Continued)

(56) References Cited

U.S. PATENT DOCUMENTS 7,120,229 B2  10/2006  Takasawa
2005/0018886 A1*  1/2005  Kim .......................... A61B 6/14
382/128

(Continued)

FOREIGN PATENT DOCUMENTS

JP  2000-107169  4/2000
JP  2005-211514  8/2005
JP  2008-12229  1/2008

*Primary Examiner* — Jingge Wu
(74) *Attorney, Agent, or Firm* — Oblon, McClelland, Maier & Neustadt, L.L.P.

(57) ABSTRACT

A medical image diagnostic apparatus according to an embodiment includes memory circuitry and processing circuitry. The memory circuitry stores therein a plurality of anatomical landmarks in a subject in association with a plurality of groups. The processing circuitry generates three-dimensional image data of the subject. The processing circuitry selects at least one group among the groups based on set examination information and a type of scan to be performed, and detects a site of the subject corresponding to at least one group, based on anatomical landmarks corresponding to a selected group. The processing circuitry controls to output information indicating a detected site.

14 Claims, 22 Drawing Sheets

(51) Int. Cl.
*G06F 19/00* (2018.01)
*A61B 6/02* (2006.01)
*A61B 6/03* (2006.01)

(52) U.S. Cl.
CPC .............. *A61B 6/032* (2013.01); *A61B 6/481* (2013.01); *A61B 6/488* (2013.01); *A61B 6/5211* (2013.01); *A61B 6/5229* (2013.01); *A61B 6/5235* (2013.01); *A61B 6/5258* (2013.01); *G06F 19/321* (2013.01); *G06T 2207/10081* (2013.01)

(58) Field of Classification Search
CPC ....... A61B 8/0875; A61B 6/503; A61B 6/504; A61B 8/00; A61B 8/5223; A61B 6/5205; A61B 6/5211; A61B 2090/3762
See application file for complete search history.

(56) References Cited

U.S. PATENT DOCUMENTS

| | | | | |
|---|---|---|---|---|
| 2009/0285357 A1* | 11/2009 | Khamene | ................ | A61B 6/08 378/20 |
| 2010/0191541 A1* | 7/2010 | Prokoski | .............. | A61B 5/0064 705/2 |
| 2011/0007954 A1* | 1/2011 | Suehling | ............ | G06K 9/00362 382/128 |
| 2011/0206260 A1* | 8/2011 | Bergmans | ............ | G01R 33/543 382/131 |
| 2011/0229005 A1* | 9/2011 | Den Harder | ......... | G06K 9/3233 382/131 |
| 2013/0155064 A1* | 6/2013 | Grbic | .................... | A61B 5/055 345/420 |
| 2014/0003695 A1* | 1/2014 | Dean | .................... | G06T 7/0012 382/131 |
| 2014/0078139 A1* | 3/2014 | Park | ....................... | G06T 7/0012 345/420 |
| 2015/0182292 A1* | 7/2015 | Hladio | ............... | A61B 17/1746 606/87 |
| 2015/0227679 A1* | 8/2015 | Kamer | .................... | G06F 19/12 703/11 |
| 2015/0228070 A1* | 8/2015 | Birkbeck | .............. | G06T 7/0012 382/131 |
| 2015/0228115 A1* | 8/2015 | Wakai | .................... | A61B 6/504 345/420 |
| 2015/0297157 A1* | 10/2015 | Mukumoto | .......... | A61B 6/5205 378/15 |
| 2016/0174902 A1* | 6/2016 | Georgescu | ................ | G06T 7/73 600/408 |
| 2016/0270853 A1* | 9/2016 | Lavallee | .................. | A61F 2/461 |
| 2018/0184997 A1* | 7/2018 | Tsukagoshi | ............ | A61B 6/032 |
| 2018/0199995 A1* | 7/2018 | Odermatt | ................. | A61B 8/00 |

* cited by examiner

FIG.5

| IDENTIFICA-TION CODE | COORDINATE | | |
|---|---|---|---|
| | POSITIONING | SCAN | |
| | | NON-CONTRAST-ENHANCED PHASE | CONTRAST-ENHANCED PHASE |
| C1 | (x1, y1, z1) | (x'1, y'1, z'1) | (x'1, y'1, z'1) |
| C2 | (x2, y2, z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ |

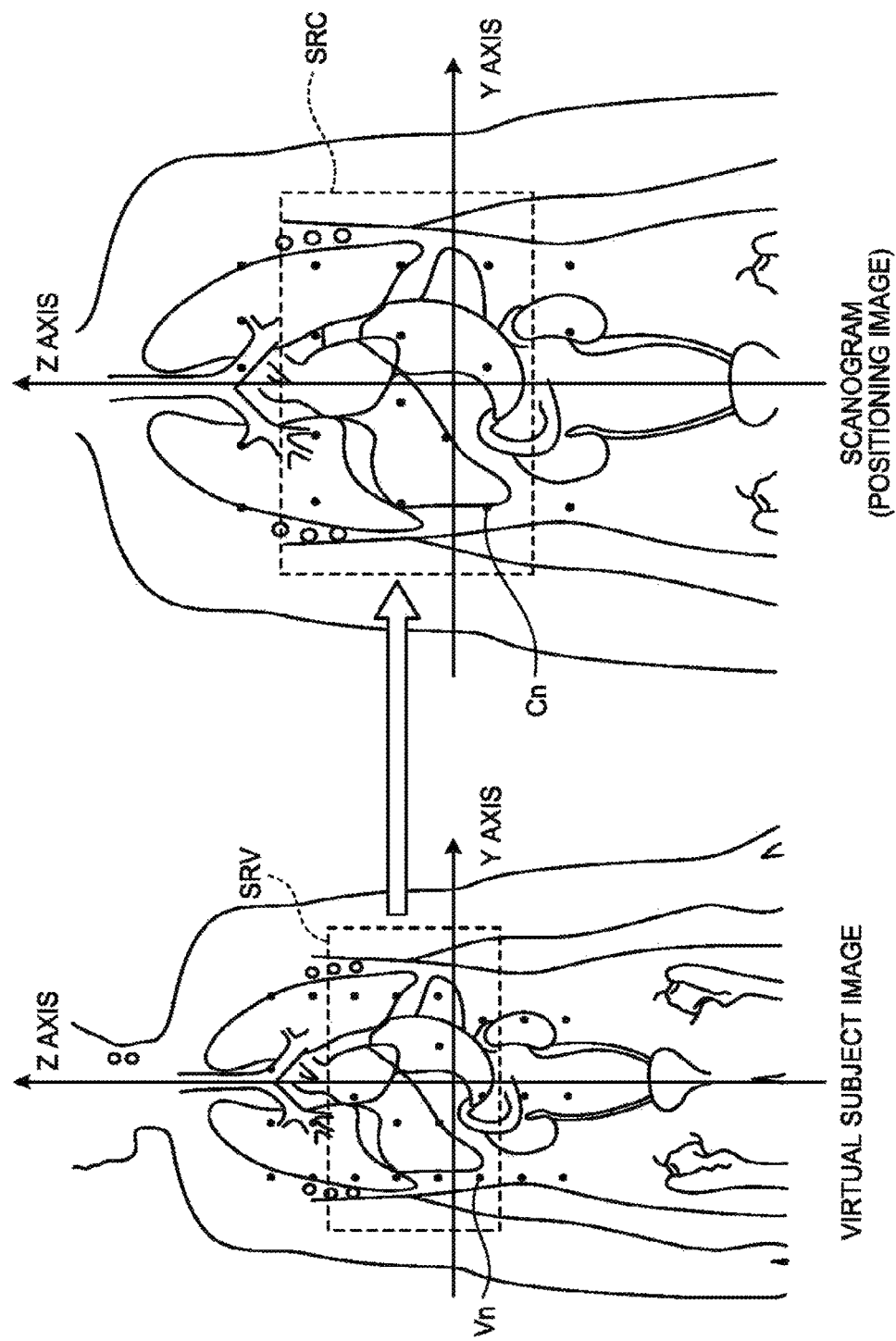

FIG.10A

| GROUP 1 POSITION | GROUP 2 INTERNAL ORGANS | GROUP 3 BONES | GROUP 4 BLOOD VESSELS | GROUP 5 NERVES |
|---|---|---|---|---|
| HEAD | BRAIN | SKULL BONE | BRAIN BLOOD VESSEL | OPTIC NERVE |
| NECK | LUNG | SHINBONE | CAROTID ARTERY | INTERCOSTAL NERVE |
| CHEST | HEART | RIB BONE | MAIN ARTERY | VENTRAL NERVE |
| ABDOMEN | LIVER | BREAST BONE | FEMORAL ARTERY | FEMORAL NERVE |
| LEGS | · | THIGHBONE | · | · |
| · | · | · | · | · |
| · | · | · | · | · |

FIG.14
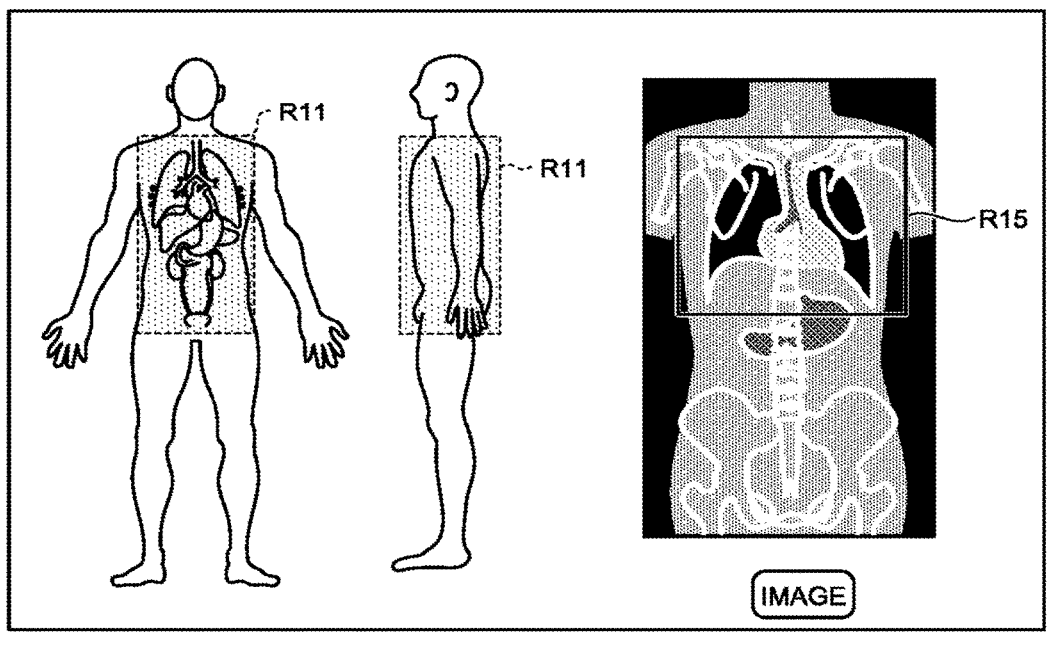
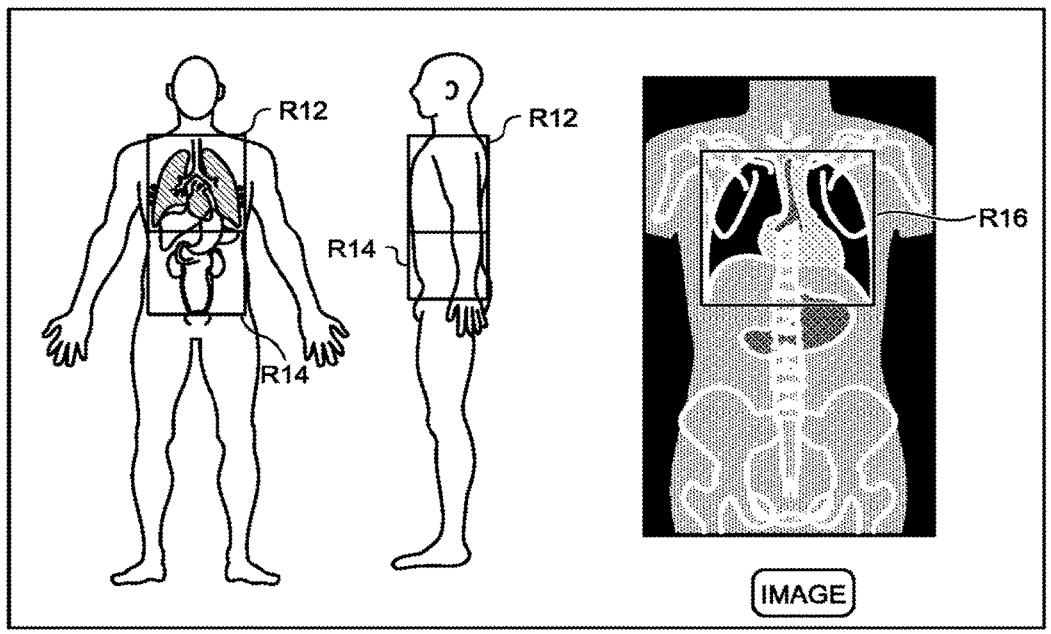

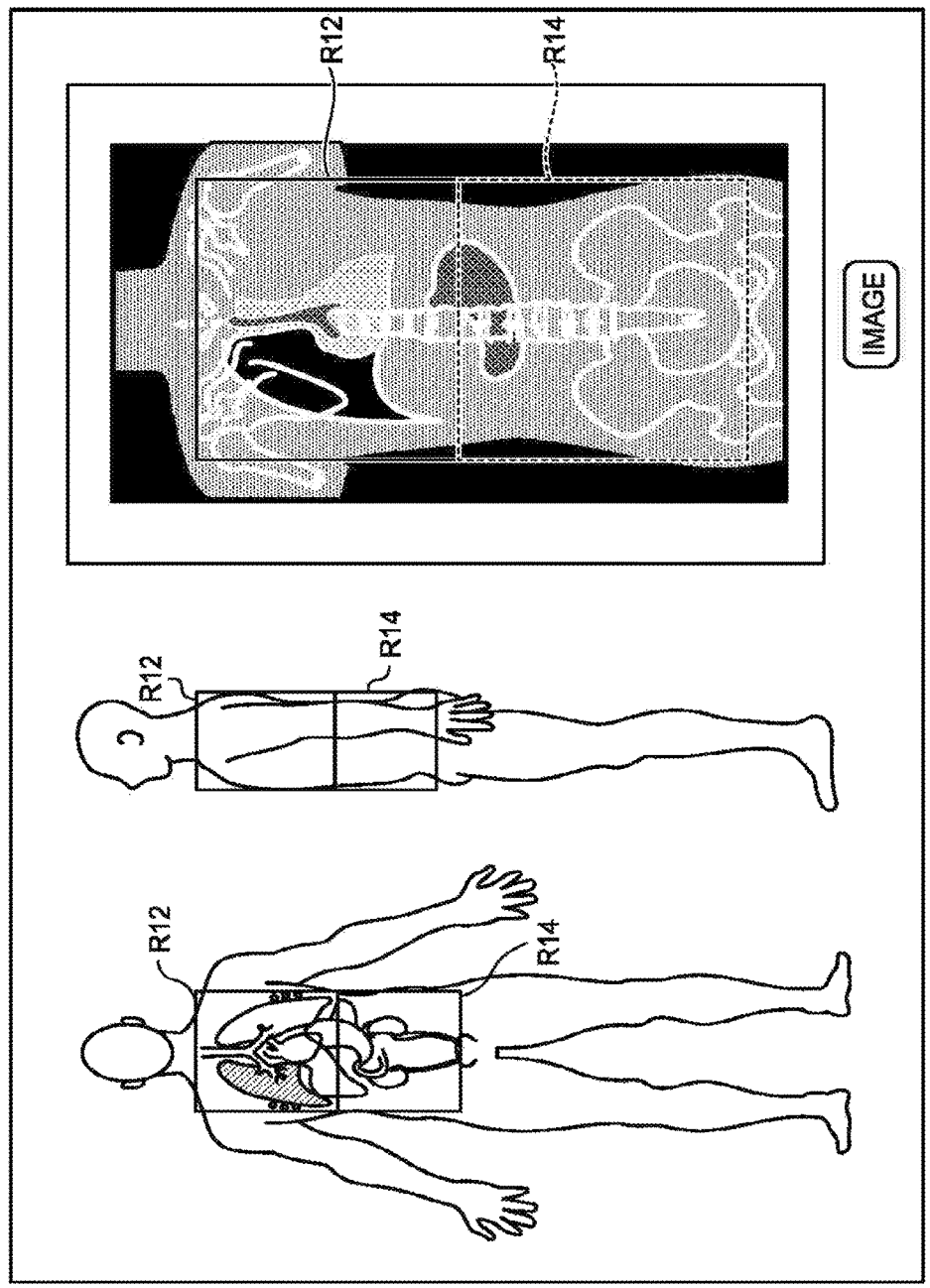

MEDICAL IMAGE DIAGNOSTIC APPARATUS

CROSS-REFERENCE TO RELATED APPLICATIONS

This application is based upon and claims the benefit of priority from Japanese Patent Application No. 2016-094081, filed on May 9, 2016, and Japanese Patent Application No. 2017-092526, filed on May 8, 2017; the entire contents of which are incorporated herein by reference.

FIELD

Embodiments described herein relate generally to a medical image diagnostic apparatus.

BACKGROUND

Conventionally, in imaging using an X-ray CT (Computed Tomography) apparatus, a scan protocol for collecting data is set depending on an examination site and examination contents. As the scan protocol, a scan protocol candidate suitable for the examination site and examination contents is selected from a plurality of preset scan protocol candidates, and a preset condition is set by being adjusted appropriately. The respective scan protocol candidates are divided depending on the age, adult/child, male/female, weight, body type such as height, and examination object. Various conditions, such as an imaging range of a positioning image (a scanogram image) for setting an imaging range, an imaging angle of the scanogram image, a tube voltage and a tube current at the time of taking the positioning image, a scan method, a scan position, and a scan range of main imaging (scanning) for collecting data to be used for diagnosis, a tube voltage and a tube current at the time of performing the scan, and the position and range in image reconstruction, are set in advance.

There has been known a method for recognizing a site included in a scanogram image and using information thereof for setting the various conditions described above. In such a method, for example, the scanogram images are collected three-dimensionally by helical scan, a site is automatically recognized based on geometric features of the collected scanogram images, and an imaging condition suitable for the recognized site is set.

BRIEF DESCRIPTION OF THE DRAWINGS

FIG. 5 is an explanatory diagram of an example of detection processing of sites performed with the detecting function according to the first embodiment;

FIG. 9 is a diagram illustrating a transformation example of a scan range by coordinate transformation according to the first embodiment;

FIG. 10A is a diagram illustrating an example of association information according to the first embodiment;

FIG. 14 is an explanatory diagram of an example of adjustment of a scan range according to the first embodiment;

FIG. 17 is a diagram illustrating an example of processing performed with a display control function according to a second embodiment.

DETAILED DESCRIPTION

According to an embodiment, a medical image diagnostic apparatus includes memory circuitry and processing circuitry. The memory circuitry is configured to store therein a plurality of anatomical landmarks in a subject in association with a plurality of groups. The processing circuitry is configured to generate three-dimensional image data of the subject. The processing circuitry is configured to select at least one group of the groups based on set examination information and a type of scan to be performed. The processing circuitry is configured to detect a site of the subject corresponding to the at least one group, based on anatomical landmarks corresponding to a selected group. The processing circuitry is configured to output information indicating a detected site.

A medical image diagnostic apparatus according to the present application will be described below with reference to the accompanying drawings. An example of a medical information processing system including an X-ray CT (Computed Tomography) apparatus as the medical image diagnostic apparatus will be described below. In a medical information processing system 100 illustrated in FIG. 1, only one server apparatus and one terminal apparatus are respectively illustrated; however, in practice, a plurality of server apparatus and terminal apparatus can be included. The medical information processing system 100 can include other medical image diagnostic apparatuses such as an X-ray diagnostic apparatus, an MRI (Magnetic Resonance Imaging) apparatus, and an ultrasonic diagnostic apparatus.

First Embodiment

Figure 1:
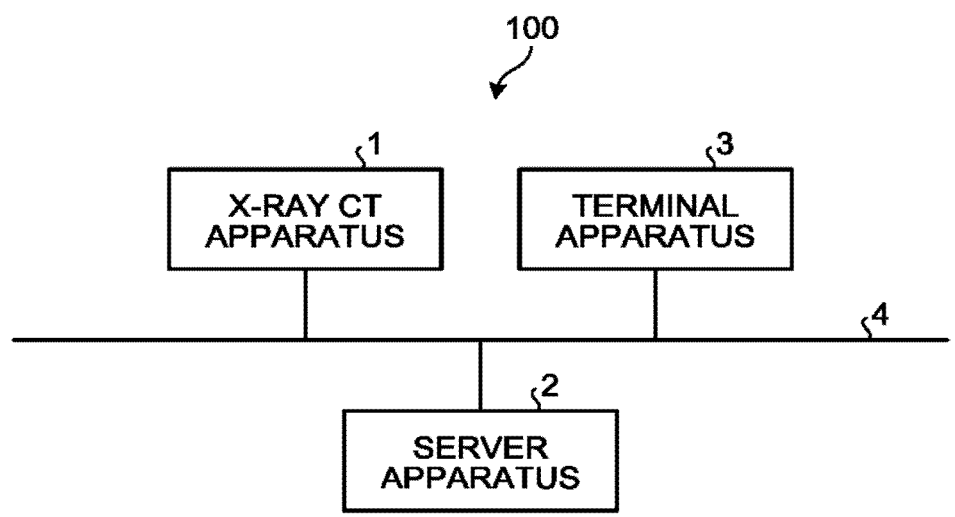
FIG. 1 is a diagram illustrating an example of a configuration of a medical information processing system according to a first embodiment.

FIG. 1 is a diagram illustrating an example of a configuration of the medical information processing system 100 according to a first embodiment. As illustrated in FIG. 1, the medical information processing system 100 according to the first embodiment includes an X-ray CT apparatus 1, a server apparatus 2, and a terminal apparatus 3. The X-ray CT apparatus 1, the server apparatus 2, and the terminal apparatus 3 are in a directly or indirectly mutually connectable state with an in-hospital LAN (Local Area Network) 4 installed in a hospital. For example, when a PACS (Picture Archiving and Communication System) is introduced in the medical information processing system 100, the respective apparatus mutually transmit and receive medical images and the like according to the DICOM (Digital Imaging and Communications in Medicine) standards.

In the medical information processing system 100, for example, an HIS (Hospital Information System) and an RIS (Radiology Information System) are introduced to manage various pieces of information. For example, the terminal apparatus 3 transmits an examination order generated along the system described above to the X-ray CT apparatus 1 and the server apparatus 2. The X-ray CT apparatus 1 acquires subject information from a subject list for each modality (a modality work list) generated according to the examination order directly received from the terminal apparatus 3 or generated by the server apparatus 2 having received the examination order, thereby collecting pieces of X-ray CT image data for each subject. The X-ray CT apparatus 1 then transmits the collected pieces of X-ray CT image data and image data generated by performing various types of image processing with respect to the X-ray CT image data to the server apparatus 2. The server apparatus 2 stores therein the pieces of X-ray CT image data and image data received from the X-ray CT apparatus 1, generates image data from the X-ray CT image data, and transmits the image data corresponding to an acquisition request from the terminal apparatus 3 to the terminal apparatus 3. The terminal apparatus 3 displays the image data received from the server apparatus 2 on a monitor or the like. The respective apparatus are described below.

The terminal apparatus 3 is an apparatus arranged in each diagnosis and treatment department in a hospital and is operated by doctors who work in each diagnosis and treatment department, and the terminal apparatus 3 is, for example, a PC (Personal Computer), a tablet PC, a PDA (Personal Digital Assistant), and a mobile phone. For example, medical chart information such as the symptom of the subject and doctor's remarks are input to the terminal apparatus 3 by the doctor. Further, an examination order for ordering an examination by the X-ray CT apparatus 1 is input to the terminal apparatus 3, and the terminal apparatus 3 transmits the input examination order to the X-ray CT apparatus 1 and the server apparatus 2. That is, the doctor in the diagnosis and treatment department operates the terminal apparatus 3, retrieves acceptance information of the subject having come to the hospital and the information of an electronic medical chart to conduct a medical examination of the subject concerned, and inputs the medical chart information to the retrieved electronic medical chart. The doctor in the diagnosis and treatment department then operates the terminal apparatus 3 to transmit the examination order, depending on the necessity of examination by the X-ray CT apparatus 1.

The server apparatus 2 is an apparatus that stores therein a medical image collected by the medical image diagnostic apparatus (for example, the X-ray CT image data and the image data collected by the X-ray CT apparatus 1) and performs various types of image processing with respect to the medical image, and is, for example, a PACS server. For example, the server apparatus 2 receives a plurality of examination orders from the terminal apparatus 3 arranged in each diagnosis and treatment department to generate a subject list for each medical image diagnostic apparatus, and transmits the generated subject list to each of the diagnosis and treatment departments. As an example, the server apparatus 2 respectively receives an examination order for conducting the examination by the X-ray CT apparatus 1 from the terminal apparatus 3 in each diagnosis and treatment department to generate the subject list, and transmits the generated subject list to the X-ray CT apparatus 1. The server apparatus 2 stores therein the X-ray CT image data and the image data collected by the X-ray CT apparatus 1, and transmits the X-ray CT image data and the image data to the terminal apparatus 3 according to an acquisition request from the terminal apparatus 3.

Figure 2:
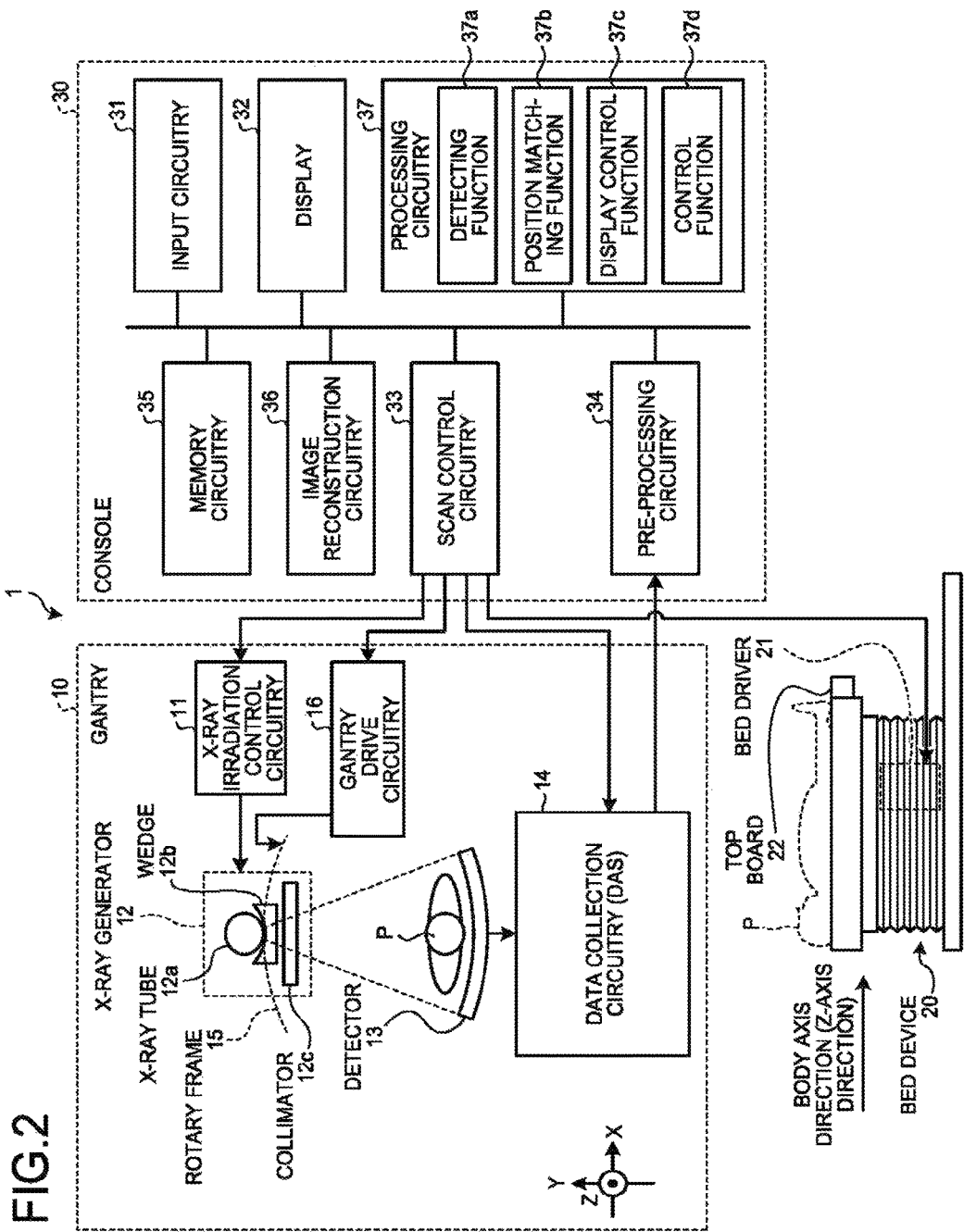
FIG. 2 is a diagram illustrating an example of a configuration of an X-ray CT apparatus according to the first embodiment.

The X-ray CT apparatus 1 collects the X-ray CT image data for each subject and transmits the collected X-ray CT image data and image data generated by performing various types of image processing to the X-ray CT image data to the server apparatus 2. FIG. 2 is a diagram illustrating an example of a configuration of the X-ray CT apparatus 1 according to the first embodiment. As illustrated in FIG. 2, the X-ray CT apparatus 1 according to the first embodiment includes a gantry 10, a bed apparatus 20, and a console 30.

The gantry 10 is an apparatus that irradiates X rays to a subject P to detect X rays having penetrated through the subject P, and outputs the detected X rays to the console 30. The gantry 10 includes X-ray irradiation control circuitry 11, an X-ray generator 12, a detector 13, data collection circuitry (DAS: Data Acquisition System) 14, a rotary frame 15, and gantry drive circuitry 16.

The rotary frame 15 is an annular frame that supports the X-ray generator 12 and the detector 13 so as to face each other, putting the subject P therebetween, and is rotated at a high speed following a circular path around the subject P by the gantry drive circuitry 16 described later.

The X-ray irradiation control circuitry 11 is an apparatus that supplies a high voltage to an X-ray tube 12a as a high-voltage generation unit. The X-ray tube 12a generates X rays by using the high voltage supplied from the X-ray irradiation control circuitry 11. The X-ray irradiation control circuitry 11 adjusts a tube voltage and a tube current to be supplied to the X-ray tube 12a under control of scan control circuitry 33 described later, so as to adjust an X-ray dosage to be irradiated to the subject P.

The X-ray irradiation control circuitry 11 also performs switching of a wedge 12b. Further, the X-ray irradiation control circuitry 11 adjusts an aperture of a collimator 12c to adjust the irradiation range (a fan angle and a cone angle) of X rays. The first embodiment can be also applied to a case where a plurality of types of wedges are switched manually by an operator.

The X-ray generator 12 is a device that generates X rays and irradiates the generated X rays to the subject P, and includes the X-ray tube 12a, the wedge 12b, and the collimator 12c.

The X-ray tube 12a is a vacuum tube that irradiates X-ray beams to the subject P by a high voltage supplied by a high-voltage generation unit (not illustrated). The X-ray tube 12a irradiates X-ray beams to the subject P with the rotation of the rotary frame 15. The X-ray tube 12a generates the X-ray beams that expands with the fan angle and the cone angle. For example, under control of the X-ray irradiation control circuitry 11, the X-ray tube 12a can continuously emit X rays around the entire circumference of the subject P for full reconstruction, or can continuously emit X rays in an exposure range capable of performing half reconstruction (180 degrees+fan angle) for half reconstruction. Further, under control of the X-ray irradiation control circuitry 11, for example, the X-ray tube 12a can intermittently emit X rays (pulse X rays) at a specific position (a tube position) set in advance. Further, the X-ray irradiation control circuitry 11 can modulate the intensity of X rays emitted from the X-ray tube 12a. For example, the X-ray irradiation control circuitry 11 raises the intensity of X rays emitted from the X-ray tube 12a at a specific tube position, and lowers the intensity of X rays emitted from the X-ray tube 12a in a range other than the specific tube position.

The wedge 12b is an X-ray filter for adjusting the X-ray dosage emitted from the X-ray tube 12a. Specifically, the wedge 12b is a filter that attenuates X rays emitted from the X-ray tube 12a so that the X-rays irradiated from the X-ray tube 12a to the subject P has a distribution set in advance. For example, the wedge 12b is a filter obtained by processing aluminum to have a predetermined target angle and a predetermined thickness. The wedge is also referred to as "wedge filter" or "bow-tie filter".

The collimator 12c is a slit for narrowing down the irradiation range of X rays with the X-ray dosage being adjusted by the wedge 12b under control of the X-ray irradiation control circuitry 11 described later.

The gantry drive circuitry 16 rotates the rotary frame 15 to turn the X-ray generator 12 and the detector 13 on the circular path around the subject P.

The detector 13 is a two-dimensional array detector (a plane detector) that detects X rays having penetrated through the subject P, in which a detection element array obtained by arranging X-ray detection elements for a plurality of channels are arranged in a plurality of rows along a body axis direction (a z-axis direction illustrated in FIG. 2) of the subject P. Specifically, the detector 13 according to the first embodiment has X-ray detection elements arrayed in multiple rows such as 320 rows along the body axis direction of the subject P, and can detect X rays having penetrated through the subject P in a wide range, for example, in a range including the lung and the heart of the subject P.

The data collection circuitry 14 is a DAS and collects projection data from the X-ray detection data detected by the detector 13. For example, the data collection circuitry 14 generates projection data by performing amplification processing, A/D conversion processing, sensitivity correction processing between channels, and the like with respect to the X-ray intensity distribution data detected by the detector 13 to generate the projection data, and transmits the generated projection data to the console 30 described later. For example, when X rays are continuously emitted from the X-ray tube 12a during rotation of the rotary frame 15, the data collection circuitry 14 collects a projection data group for the entire circumference (for 360 degrees). The data collection circuitry 14 also transmits the tube position in association with the respective pieces of collected projection data to the console 30 described later. The tube position is information indicating the projection direction of the projection data. The sensitivity correction processing between the channels can be performed by pre-processing circuitry 34 described later.

The bed device 20 is a device for placing the subject P thereon, and as illustrated in FIG. 2, includes a bed driver 21 and a top board 22. The bed driver 21 moves the top board 22 in the Z-axis direction to move the subject P into the rotary frame 15. The top board 22 is a board on which the subject P is placed.

The gantry 10 performs helical scan in which the rotary frame 15 is, for example, rotated while moving the top board 22 to scan the subject P helically. Alternatively, the gantry 10 performs conventional scan in which after the top board 22 is moved, the rotary frame 15 is rotated with the position of the subject P being fixed to scan the subject P along the circular path. Alternatively, the gantry 10 executes a step-and-shoot method in which the conventional scan is performed in a plurality of scan areas, while moving the position of the top board 22 at a regular interval.

The console 30 is a device that receives an operation of the X-ray CT apparatus by an operator, and reconstructs the X-ray CT image data by using the pieces of projection data collected by the gantry 10. The console 30 includes, as illustrated in FIG. 2, input circuitry 31, a display 32, the scan control circuitry 33, the pre-processing circuitry 34, memory circuitry 35, image reconstruction circuitry 36, and processing circuitry 37.

The input circuitry 31 has a mouse, a keyboard, a trackball, a switch, a button, a joy stick, and the like, and transfers an instruction and setting information received from the operator to the processing circuitry 37. For example, the input circuitry 31 receives imaging conditions of the X-ray CT image data, reconstruction conditions at the time of reconstructing the X-ray CT image data, image processing conditions with respect to the X-ray CT image data, and the like from the operator. Further, the input circuitry 31 receives an operation for selecting the examination with respect to the subject. The input circuitry 31 also receives a designation operation for designating a site on the image.

The display 32 is a monitor referred to by the operator, and displays image data generated from the X-ray CT image data to the operator, and displays a GUI (Graphical User Interface) for receiving various instructions and various settings from the operator via the input circuitry 31, under control of the processing circuitry 37. The display 32 also displays a planning screen for a scan plan, and a screen during the scan. Further, the display 32 displays a virtual subject image including exposure information and image data. The virtual subject image displayed on the display 32 is described later in detail.

The scan control circuitry 33 controls the operations of the X-ray irradiation control circuitry 11, the gantry drive circuitry 16, the data collection circuitry 14, and the bed driver 21 under control of the processing circuitry 37, thereby controlling the collection processing of the projection data in the gantry 10. Specifically, the scan control circuitry 33 respectively controls the collection processing of the projection data in imaging for collecting positioning images (scanogram images) and main imaging (scan) for collecting images to be used for diagnosis. In the X-ray CT apparatus 1 according to the first embodiment, a two-dimensional scanogram image and a three-dimensional scanogram image can be taken.

For example, the scan control circuitry 33 takes the two-dimensional scanogram image by fixing the X-ray tube 12a at a position of 0 degree (at a position in a front direction relative to the subject) and continuously performing imaging while moving the top board at a constant speed. Alternatively, the scan control circuitry 33 takes the two-dimensional scanogram image by intermittently repeating imaging in synchronization with the movement of the top board, while fixing the X-ray tube 12a at the position of 0 degree and intermittently moving the top board. The scan control circuitry 33 can take the positioning image not only in the front direction relative to the subject but also in arbitrary directions (for example, from a side direction).

Figure 3:
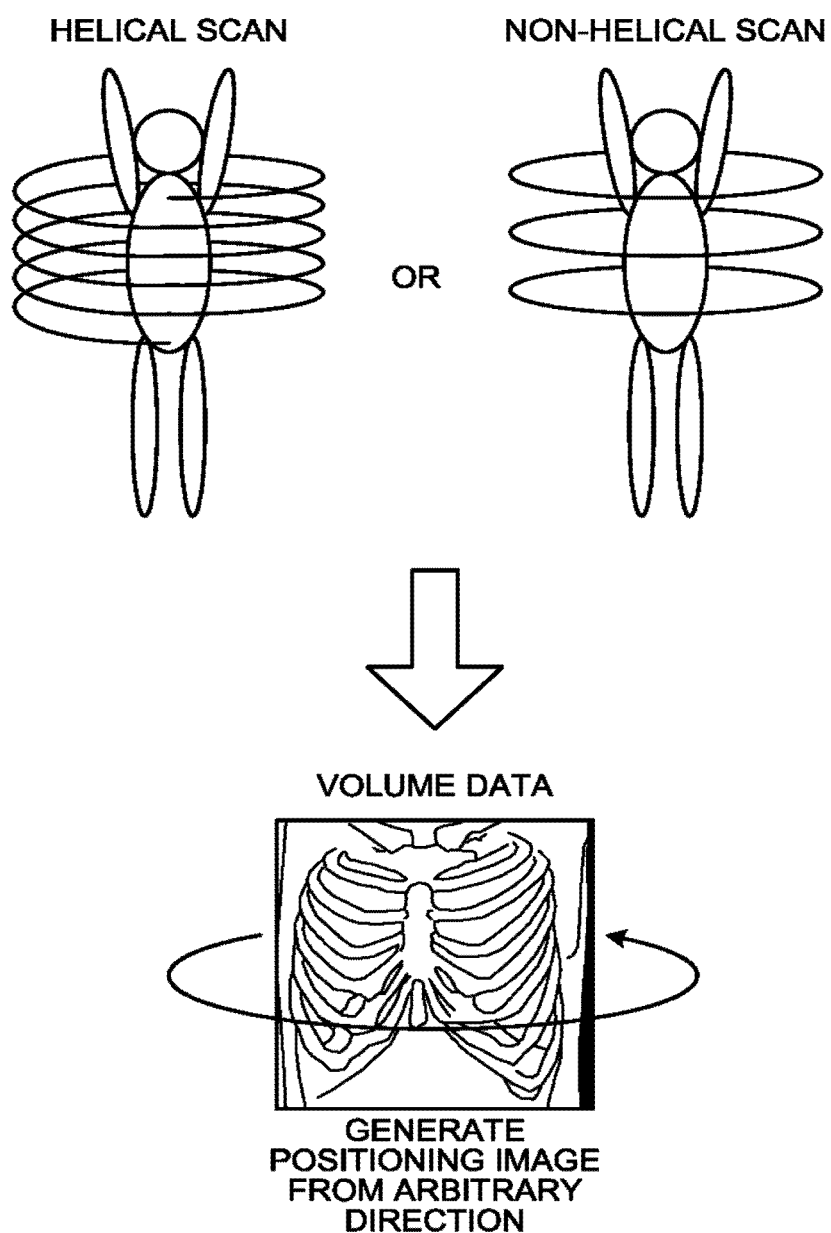
FIG. 3 is an explanatory diagram of taking a three-dimensional scanogram image by scan control circuitry according to the first embodiment.

The scan control circuitry 33 takes the three-dimensional scanogram image by collecting the pieces of projection data for the entire circumference with respect to the subject, in imaging of the scanogram image. FIG. 3 is an explanatory diagram of taking a three-dimensional scanogram image by the scan control circuitry 33 according to the first embodiment. For example, the scan control circuitry 33 collects the pieces of projection data for the entire circumference with respect to the subject by the helical scan or non-helical scan, as illustrated in FIG. 3. The scan control circuitry 33 performs the helical scan or non-helical scan with a less dosage than the dosage in the main imaging, with respect to a wide range such as the entire chest, the entire abdomen, the entire upper body, or the entire body of the subject. As the non-helical scan, for example, the step-and-shoot scan described above is performed.

As described above, because the scan control circuitry 33 collects the pieces of projection data for the entire circumference with respect to the subject, the image reconstruction circuitry 36 described later can reconstruct three-dimensional X-ray CT image data (volume data), thereby enabling to generate the positioning image from an arbitrary direction by using the reconstructed volume data, as illustrated in FIG. 3. An operator can set arbitrarily whether to take the positioning image by two-dimensional imaging or three-dimensional imaging, or it can be set in advance according to the examination contents.

Referring back to FIG. 2, the pre-processing circuitry 34 performs logarithmic conversion, offset correction, and correction processing such as sensitivity correction, and beam hardening correction with respect to the projection data generated by the data collection circuitry 14, thereby generating corrected projection data. Specifically, the pre-processing circuitry 34 generates the corrected projection data for each of the projection data of the positioning image generated by the data collection circuitry 14 and the pieces of projection data collected by the main imaging, and stores the respective pieces of corrected projection data in the memory circuitry 35.

The memory circuitry 35 stores therein the projection data generated by the pre-processing circuitry 34. Specifically, the memory circuitry 35 stores therein the projection data of the positioning image and the projection data for diagnosis collected by the main imaging, which have been generated by the pre-processing circuitry 34. Further, the memory circuitry 35 stores therein the image data and the virtual subject image generated by the image reconstruction circuitry 36 described later. The memory circuitry 35 appropriately stores therein processing results obtained by the processing circuitry 37 described later. The memory circuitry 35 also stores therein association information described later. The virtual subject image, the processing results by the processing circuitry 37, and the association information are described later. The memory circuitry 35 is an example of a memory circuitry described in the claims.

The image reconstruction circuitry 36 reconstructs the X-ray CT image data by using the projection data stored in the memory circuitry 35. Specifically, the image reconstruction circuitry 36 reconstructs X-ray CT image data respectively from the projection data of the positioning image and the projection data of the image used for diagnosis. As the reconstruction method, various methods can be considered, and for example, back projection can be mentioned. As the back projection, for example, back projection by using an FBP (Filtered Back Projection) method can be mentioned. Alternatively, the image reconstruction circuitry 36 can reconstruct X-ray CT image data by using successive approximation.

The image reconstruction circuitry 36 performs various types of image processing with respect to the X-ray CT image data, thereby generating image data. The image reconstruction circuitry 36 stores the reconstructed X-ray CT image data and the image data generated by performing various types of image processing in the memory circuitry 35. The image reconstruction circuitry 36 is an example of a reconstruction circuitry described in the claims.

The processing circuitry 37 controls the operations of the gantry 10, the bed device 20, and the console 30 to execute the entire control of the X-ray CT apparatus 1. Specifically, the processing circuitry 37 controls CT scan performed on the gantry 10 by controlling the scan control circuitry 33. The processing circuitry 37 also controls image reconstruction processing and image generation processing in the console 30 by controlling the image reconstruction circuitry 36. Further, the processing circuitry 37 controls to display respective types of image data stored in the memory circuitry 35 on the display 32.

The processing circuitry 37 performs a detecting function 37a, a position matching function 37b, a display control function 37c, and a control function 37d as illustrated in FIG. 2. For example, the respective processing functions executed by the detecting function 37a, the position matching function 37b, the display control function 37c, and the control function 37d being constituent elements of the processing circuitry 37 illustrated in FIG. 2 are recorded in the memory circuitry 35 in the form of programs executable by a computer. The processing circuitry 37 is a processor that realizes the functions corresponding to the respective programs by retrieving the respective programs from the memory circuitry 35 and executing the respective programs. In other words, the processing circuitry 37 after having retrieved the respective programs has the respective functions illustrated in the processing circuitry 37 in FIG. 2. The processing circuitry 37 described in the first embodiment is an example of a processing circuitry described in the claims.

The word "processor" used in the above descriptions means a CPU (Central Processing Unit), a GPU (Graphics Processing Unit), or a circuit such as an application specific integrated circuit (ASIC), a programmable logic device (for example, a simple programmable logic device (SPLD), a complex programmable logic device (CPLD), and a field programmable GateArray (FPGA). The processor retrieves and executes the programs saved in the memory circuitry to realize the respective functions. Instead of saving the program in the memory circuitry, the programs can be directly installed in the circuit of the processor. In this case, the processor retrieves and executes the programs installed in the circuit to realize the respective functions. The respective processors according to the first embodiment are not limited to a case configured as a single circuit for each processor, and can be configured as one processor by combining a plurality of independent circuits to realize the functions thereof.

The detecting function 37a respectively detects a plurality of sites in the subject included in the three-dimensional image data. Specifically, the detecting function 37a detects sites such as internal organs included in the three-dimensional X-ray CT image data (volume data) reconstructed by the image reconstruction circuitry 36. For example, the detecting function 37a detects sites such as the internal organs based on anatomical landmarks, for at least one of the volume data of the positioning image and the volume data of the image used for diagnosis. The anatomical landmarks are points indicating features of sites such as a specific bone, internal organ, blood vessel, nerve, and lumen. That is, the detecting function 37a detects the anatomical landmark such as a specific internal organ or bone to detect the bone, the internal organ, the blood vessel, the nerve, and the lumen included in the volume data. Further, the detecting function 37a can detect positions of the head, the neck, the chest, the abdomen, and the legs by detecting the anatomical landmarks of a human body. The sites described in the first embodiment mean sites including these positions in addition to the bones, the internal organs, the blood vessels, the nerves, and the lumen. An example of detection of a site by the detecting function 37a is described below.

For example, the detecting function 37a extracts the anatomical landmark from a voxel value included in the volume data, in the volume data of the positioning image or the volume data of the image used for diagnosis. The detecting function 37a compares a position of the landmark extracted from the volume data with a three-dimensional position of the anatomical landmark in the information such as in a textbook, and removes an inaccurate landmark from the landmarks extracted from the volume data to optimize the positions of the landmarks extracted from the volume data. Accordingly, the detecting function 37a detects respective sites of the subject included in the volume data. As an example, the detecting function 37a first extracts anatomical landmarks included in the volume data by using a taught machine learning algorithm. The taught machine learning algorithm is constructed by using a plurality of teaching images in which accurate anatomical landmarks are manually arranged, and for example, a decision forest is used.

The detecting function 37a compares the extracted landmark with a model indicating a three-dimensional position relation of the anatomical landmarks in the body, thereby optimizing the extracted landmarks. The model described above is constructed by using the teaching images, and for example, a point distribution model is used. That is, the detecting function 37a compares the extracted landmark with a model in which the shape and the position relation of the site, and a point unique to the site are defined based on a plurality of teaching images in which accurate anatomical landmarks are manually arranged to remove an inaccurate landmark from the landmarks, thereby optimizing the landmarks.

Figure 4A:
FIG. 4A is an explanatory diagram of an example of detection processing of sites performed with a detecting function according to the first embodiment.
Figure 4B:
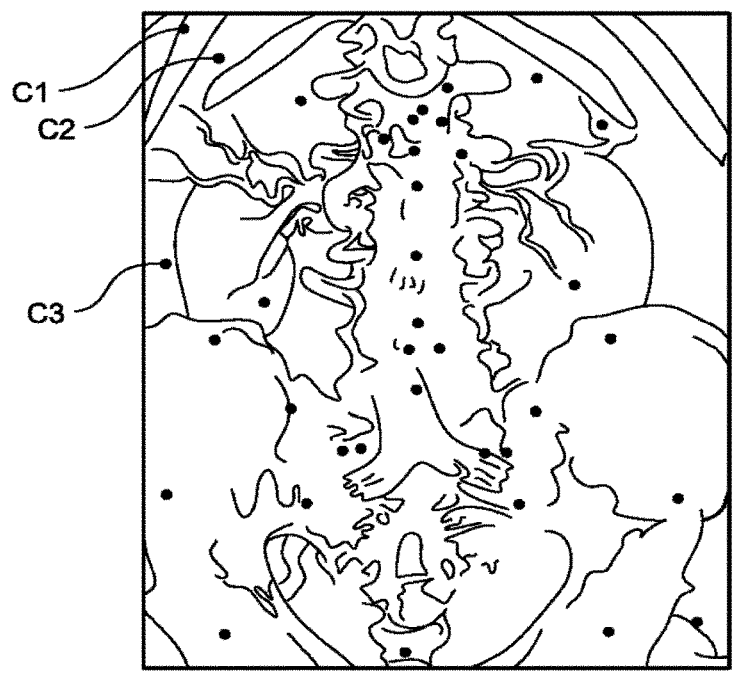
FIG. 4B is an explanatory diagram of an example of detection processing of sites performed with the detecting function according to the first embodiment.

An example of the detection processing of sites performed with the detecting function 37a is described below, with reference to FIGS. 4A, 4B, 5, and 6. FIGS. 4A, 4B, 5, and 6 are explanatory diagrams of an example of the detection processing of sites performed with the detecting function 37a according to the first embodiment. In FIG. 4A and FIG. 4B, landmarks are arranged two-dimensionally; however, in practice, the landmarks are arranged three-dimensionally. For example, the detecting function 37a applies the taught machine learning algorithm to the volume data to extract voxels regarded as the anatomical landmarks (black points in FIG. 4A) as illustrated in FIG. 4A. The detecting function 37a removes the inaccurate landmarks from the extracted voxels, as illustrated in FIG. 4B, by fitting the positions of the extracted voxels to the model in which the shape and the position relation of the site, and the points unique to the site are defined, thereby extracting only the voxels corresponding to more accurate landmarks.

The detecting function 37a adds an identification code for identifying the landmarks indicating the features of the respective sites to the extracted landmarks (voxels), and stores information in which the identification code is associated with the position (coordinate) information of the respective landmarks in the memory circuitry 35, while being accompanied by the image data. For example, the detecting function 37a adds the identification code such as C1, C2 and C3 respectively to the extracted landmarks (voxels), as illustrated in FIG. 4B. The detecting function 37a adds the identification code respectively to each data having subjected to the detection processing, which is then stored in the memory circuitry 35. Specifically, the detecting function 37a detects a site of the subject included in the volume data reconstructed from at least one projection data, of the projection data of the positioning image, the projection data collected in a non-contrast-enhanced manner, and the projection data collected in a contrast-enhanced state by a contrast agent.

For example, the detecting function 37a stores information in which the identification codes are associated with the coordinates of the respective voxels detected from the volume data of the positioning image (in FIG. 5, positioning) in the memory circuitry 35, while being accompanied by the volume data. As an example, the detecting function 37a extracts the coordinates of the landmarks from the volume data of the positioning image, and as illustrated in FIG. 5, stores "identification code: C1, coordinate $(x_1, y_1, z_1)$", "identification code: C2, coordinate $(x_2, y_2, z_2)$", and the like in association with the volume data in the memory circuitry 35. Accordingly, the detecting function 37a can identify what type of landmark is at which position in the volume data of the positioning image, and can detect respective sites such as the internal organs based on these pieces of information.

For example, as illustrated in FIG. 5, the detecting function 37a stores the information in which the identification code is associated with the coordinates of the respective voxels detected from the volume data of the image for diagnosis (in FIG. 5, scan) in the memory circuitry 35, while being accompanied by the volume data. In the scan, the detecting function 37a can extract the coordinates of the landmarks respectively from the volume data contrast-enhanced by the contrast agent (in FIG. 5, contrast-enhanced phase), and the volume data that is not contrast-enhanced by the contrast agent (in FIG. 5, non-contrast-enhanced phase), and associate the identification code with the extracted coordinates.

As an example, the detecting function 37a extracts the coordinate of the landmark from the volume data in the non-contrast-enhanced phase, of the volume data of the image for diagnosis, and as illustrated in FIG. 5, stores in the memory circuitry 35 "identification code: C1, coordinate $(x'_1, y'_1, z'_1)$", "identification code: C2, coordinate $(x'_2, y'_2, z'_2)$", and the like in association with the volume data.

Further, the detecting function 37a extracts the coordinate of the landmark from the volume data in the contrast-enhanced phase, and as illustrated in FIG. 5, stores in the memory circuitry 35 "identification code: C1, coordinate $(x'_1, y'_1, z'_1)$", "identification code: C2, coordinate $(x'_2, y'_2, z'_2)$", and the like in association with the volume data. In the case where the landmark is to be extracted from the volume data in the contrast-enhanced phase, landmarks that can be extracted by being contrast-enhanced are included. Therefore, in the case of the volume data in the contrast-enhanced phase, the blood vessels contrast-enhanced by the contrast agent can be extracted. Therefore, in the case of the volume data in the contrast-enhanced phase, as illustrated in FIG. 5, the detecting function 37a associates the identification codes C31, C32, C33, and C34 for identifying the respective blood vessels with the coordinate $(x'_{31}, y'_{31}, z'_{31})$ to the coordinate $(x'_{34}, y'_{34}, z'_{34})$ of the landmarks such as blood vessels extracted by being contrast-enhanced.

As described above, the detecting function 37a can identify what type of landmark is at which position in the volume data of the positioning image or the image for diagnosis, and can detect respective sites such as the internal organs based on these pieces of information. For example, the detecting function 37a detects the position of a target site to be detected by using information of an anatomical position relation between the target site and a peripheral site of the target site. As an example, when the target site is the "lung", the detecting function 37a acquires coordinate information associated with the identification code indicating a feature of the lung, and acquires coordinate information associated with the identification codes indicating the peripheral site of the "lung", such as the "rib", "collarbone", "heart", and "diaphragm". The detecting function 37a extracts the "lung" region in the volume data by using the information of the anatomical position relation between the "lung" and the peripheral site and the acquired pieces of coordinate information.

Figure 6:
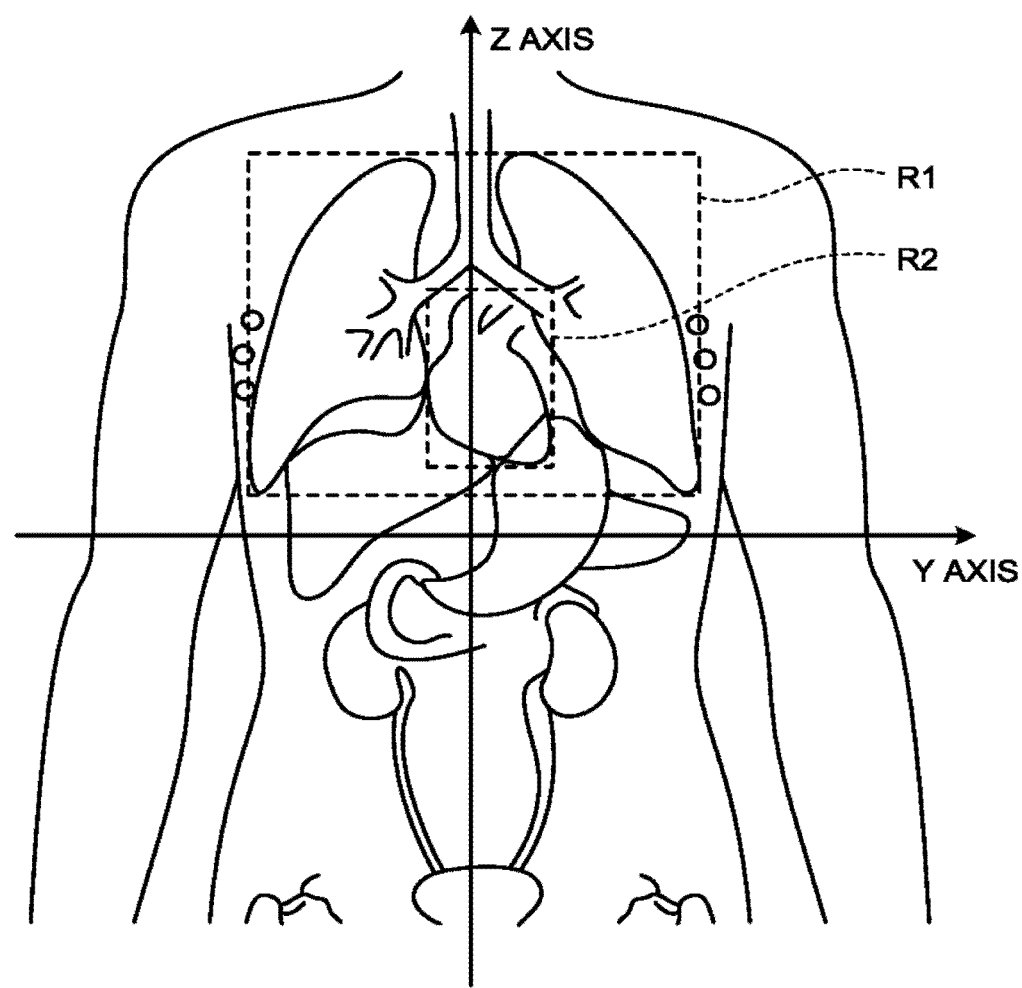
FIG. 6 is an explanatory diagram of an example of detection processing of sites performed with the detecting function according to the first embodiment.

For example, the detecting function 37a extracts a region R1 corresponding to the "lung" in the volume data, as illustrated in FIG. 6, from the information of the position relation such as "apex of lung: 2 to 3 centimeters above the collarbone" and "lower end of the lung: height of the seventh rib" and the coordinate information of respective sites. That is, the detecting function 37a extracts the coordinate information of the voxels in the region R1 in the volume data. The detecting function 37a stores the extracted coordinate information in association with the site information in the memory circuitry 35, while being accompanied by the volume data. Similarly, the detecting function 37a can extract a region R2 corresponding to the "heart" in the volume data, as illustrated in FIG. 6.

Further, the detecting function 37a detects the positions included in the volume data, based on landmarks defining the positions of the head, the chest, and the like in the human body. The positions of the head, the chest, and the like in the human body can be defined arbitrarily. For example, if the chest is defined to be from the seventh cervical spine to the lower end of the lung, the detecting function 37a detects a site from the landmark corresponding to the seventh cervical spine to the landmark corresponding to the lower end of the lung as the chest. The detecting function 37a can detect sites according to various methods, other than the method of using the anatomical landmarks described above. For example, the detecting function 37a can detect sites included in the volume data by a region expansion method based on the voxel value.

The position matching function 37b matches respective positions of a plurality of sites in the subject included in the three-dimensional image data with respective positions of a plurality of sites in the human body included in the virtual subject data. The virtual subject data is information representing standard positions of the respective sites in the human body. That is, the position matching function 37b matches the sites of the subject with the positions of standard sites, and stores the matching results in the memory circuitry 35. For example, the position matching function 37b matches a virtual subject image in which sites of the human body are arranged at standard positions with the volume data of the subject.

The virtual subject data is described first. The virtual subject data is generated beforehand as an image obtained by actually imaging a human body having a standard physical size with X rays, corresponding to a plurality of combinations relevant to parameters in regard to the age, adult/child, male/female, and the physical size such as weight and height, and is stored in the memory circuitry 35. That is, the memory circuitry 35 stores therein pieces of data of a plurality of virtual subject images corresponding to the combinations of the parameters described above. The virtual subject images stored in the memory circuitry 35 is associated with the anatomical landmarks (landmarks) and stored. For example, the human body has many anatomical landmarks that can be extracted relatively easily from the image, based on morphological features and the like by image processing such as pattern recognition. The positions and arrangement of these anatomical landmarks in the body are approximately decided depending on the age, adult/child, male/female, and the physical size such as weight and height.

Figure 7:
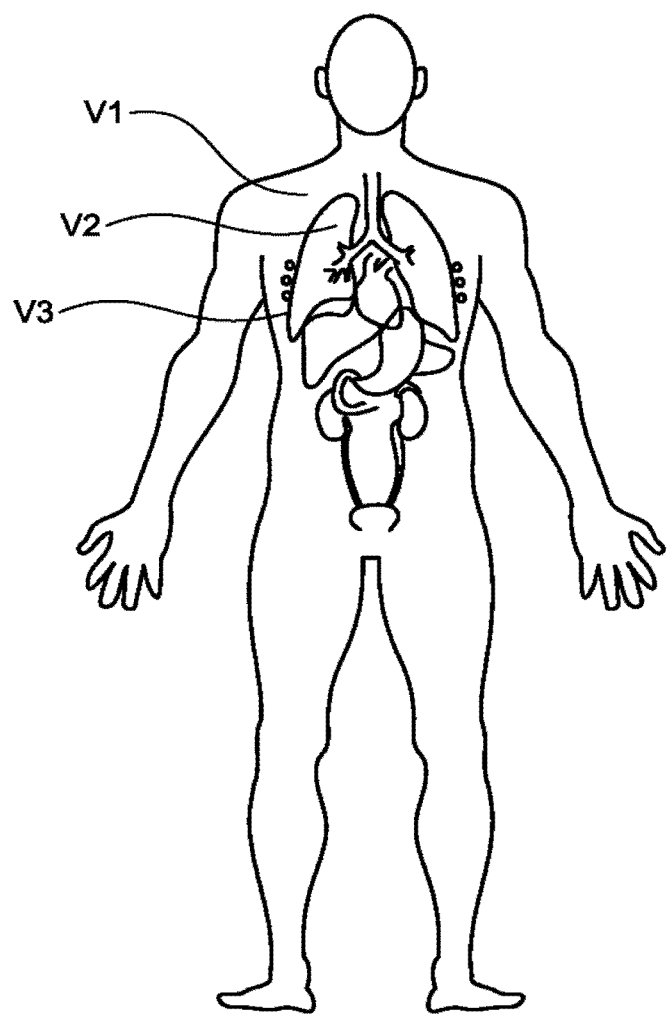
FIG. 7 is a diagram illustrating an example of a virtual subject image stored in memory circuitry according to the first embodiment.

In the virtual subject image stored in the memory circuitry 35, many anatomical landmarks are detected beforehand, and position data of the detected landmarks is stored in the memory circuitry 35 accompanied by or associated with the data of the virtual subject image, together with the identification codes of the respective landmarks. FIG. 7 is a diagram illustrating an example of the virtual subject image stored in the memory circuitry 35 according to the first embodiment. For example, as illustrated in FIG. 7, the memory circuitry 35 stores therein the virtual subject image in which the anatomical landmarks and identification codes "V1", "V2", and "V3" for identifying the landmarks are associated with a three-dimensional human body including sites such as the internal organs.

That is, the memory circuitry 35 stores therein the coordinates of the landmarks in a coordinate space of a three-dimensional human image and the corresponding identification codes in association with each other. As an example, the memory circuitry 35 stores therein the coordinate of the landmark corresponding to the identification code "V1" illustrated in FIG. 7 in association therewith. Similarly, the memory circuitry 35 stores therein the coordinate of the landmark and the identification code in association therewith. In FIG. 7, although only the lung, the heart, the liver, the stomach, and the kidney are illustrated as the internal organs, more internal organs, bones, blood vessels and nerves are actually included in the virtual subject image. Further, in FIG. 7, only the landmarks corresponding to the identification codes "V1", "V2", and "V3" are illustrated. However, more landmarks are included in practice.

Figure 8:
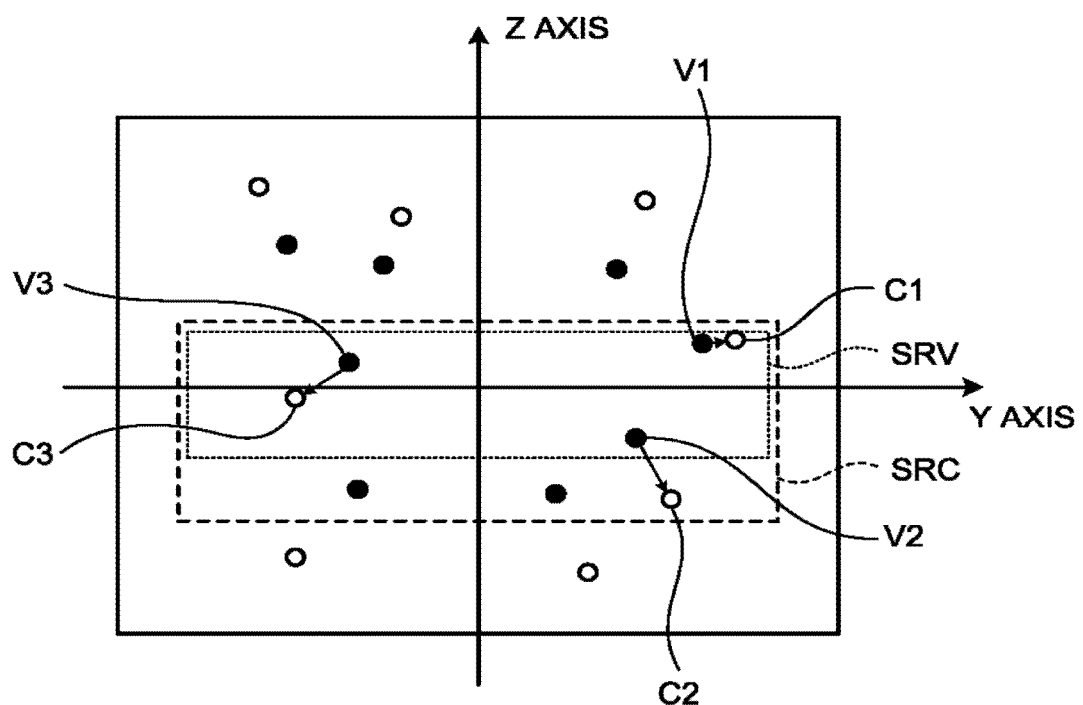
FIG. 8 is an explanatory diagram of an example of matching processing with a position matching function according to the first embodiment.

The position matching function 37b matches the landmarks in the volume data of the subject detected by the detecting function 37a with the landmarks in the virtual subject image described above by using the identification codes, thereby associating the coordinate space of the volume data with the coordinate space of the virtual subject image. FIG. 8 is an explanatory diagram of an example of the matching processing with the position matching function 37b according to the first embodiment. In FIG. 8, a case where matching is performed by using three pairs of landmarks allocated with the identification codes respectively indicating the same landmark between the landmarks detected from the scanogram image and the landmarks detected from the virtual subject image. However, the first embodiment is not limited thereto, and matching can be performed by using arbitrary pairs of landmarks.

For example, as illustrated in FIG. 8, when the landmarks indicated by the identification codes "V1", "V2", and "V3" in the virtual subject image and the landmarks indicated by the identification codes "C1", "C2", and "C3" in the scanogram image are matched with each other, the position matching function 37b performs coordinate transformation so as to minimize a position gap between the same landmarks, thereby associating the coordinate spaces between the images. For example, the position matching function 37b obtains the following coordinate transformation matrix "H" so as to minimize the sum "LS" of position gaps between the anatomically same landmarks "V1(x1, y1, z1), C1(X1, Y1, Z1)", "V2(x2, y2, z2), C2(X2, Y2, 21)", and "V3(x3, y3, 31), C3(X3, Y3, Z3)".

$$LS=((X1,Y1,Z1)-H(x1,y1,z1))+((X2,Y2,Z2)-H(x2,y2,z2))+((X3,Y3,Z3)-H(x3,y3,z3))$$

The position matching function 37b can transform a scan range specified on the virtual subject image to a scan range on the positioning image by the obtained coordinate transformation matrix "H". For example, as illustrated in FIG. 8, the position matching function 37b can transform a scan range "SRV" specified on the virtual subject image to a scan range "SRC" on the positioning image by using the coordinate transformation matrix "H". FIG. 9 is a diagram illustrating a transformation example of the scan range by coordinate transformation according to the first embodiment. For example, as illustrated on the virtual subject image in FIG. 9, when an operator sets the scan range "SRV" on the virtual subject image, the position matching function 37b uses the coordinate transformation matrix described above to transform the set scan range "SRV" to the scan range "SRC" on the scanogram image.

Accordingly, for example, the scan range "SRV" set to include the landmark corresponding to the identification code "Vn" on the virtual subject image is transformed to the scan range "SRC" including the identification code "Cn" corresponding to the same landmark on the scanogram image, and set. The coordinate transformation matrix "H" described above can be stored in the memory circuitry 35 for each subject, appropriately retrieved from the memory circuitry 35 and used. Alternatively, the coordinate transformation matrix "H" can be calculated every time the scanogram image is collected. In this manner, according to the first embodiment, the virtual subject image is displayed for specifying the range at the time of presetting, and the position and the range are planned thereon. Accordingly, after taking the positioning image (scanogram image), the position and the range on the positioning image corresponding to the planned position and range can be automatically set by using numerical values.

Referring back to FIG. 2, the display control function 37c controls so as to display various pieces of display information on the display 32. For example, the display control function 37c controls to display various types of image data stored in the memory circuitry 35 on the display 32. Further, the display control function 37c controls to display information according to the detection result by the detecting function 37a on the display 32. Details of information displayed under control of the display control function 37c are described later. The control function 37d controls the operations of the gantry 10, the bed device 20, and the console 30 to execute the entire control of the X-ray CT apparatus 1. Specifically, the control function 37d controls the scan control circuitry 33 to control CT scan performed on the gantry 10. Further, the control function 37d controls the image reconstruction circuitry 36 to control the image reconstruction processing and the image generation processing in the console 30. The control executed by the control function 37d is described later in detail.

An overall configuration of the X-ray CT apparatus 1 according to the first embodiment has been described above. In such a configuration, the X-ray CT apparatus 1 according to the first embodiment enables to perform site detection efficiently. Specifically, the X-ray CT apparatus 1 stores the association information in which the plurality of anatomical landmarks are associated with the plurality of groups beforehand in the memory circuitry, and selects a group based on the examination information and the type of scan. The X-ray CT apparatus 1 refers to the association information to detect the site of the landmark corresponding to the selected group, thereby enabling to perform site detection efficiently. In selection of the group, the X-ray CT apparatus 1 can select a group associated beforehand with the examination information and the type of scan. Further, in selection of the group, the X-ray CT apparatus 1 can select a group based on the examination information and the priority of the group for each type of scan. A case in which a group associated beforehand with the examination information and the type of scan is selected, and a case in which a group is selected based on the examination information and the priority of the group for each type of scan is described in this order.

Figure 10B:
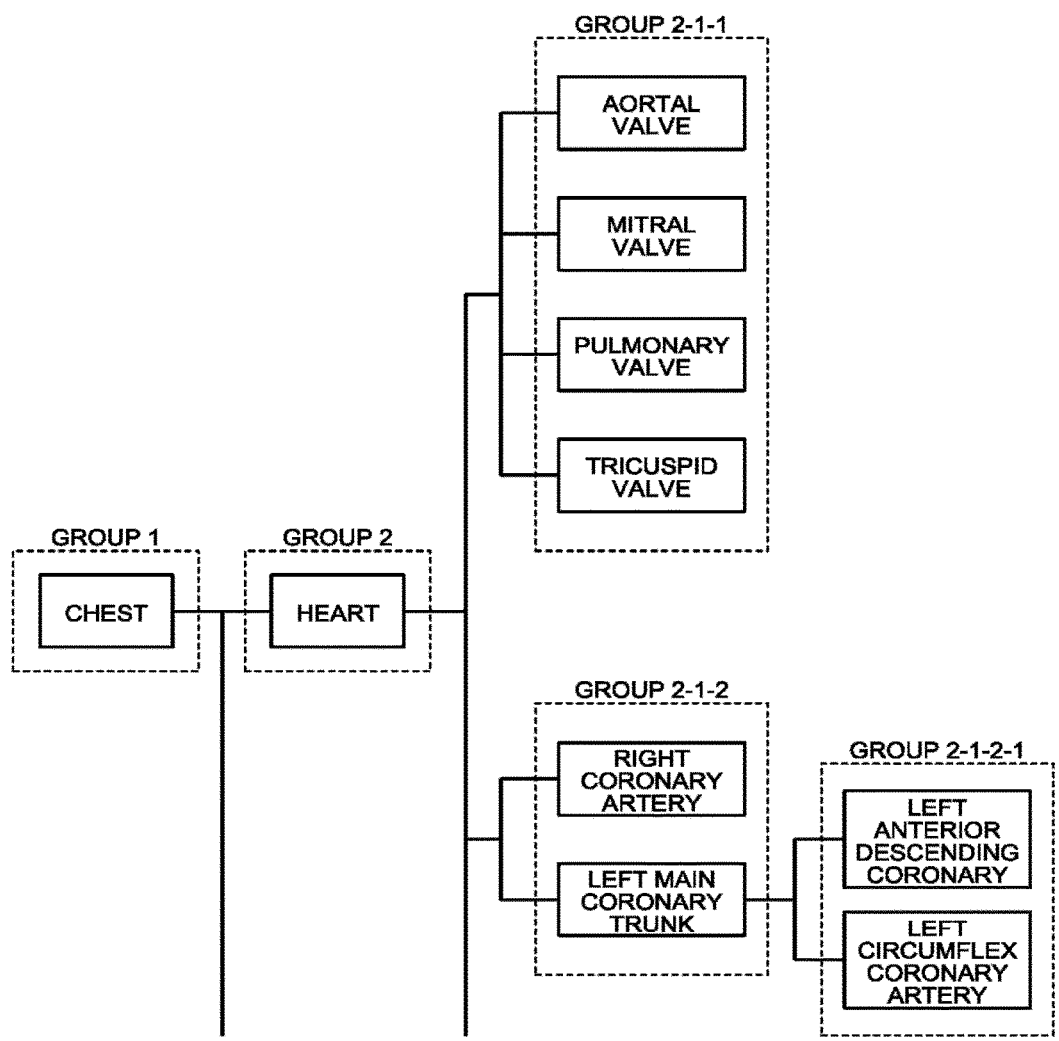
FIG. 10B is a diagram illustrating an example of the association information according to the first embodiment.

The case in which a group associated beforehand with the examination information and the type of scan is selected is described first. First, in the X-ray CT apparatus 1, the memory circuitry 35 stores therein the association information in which the plurality of anatomical landmarks in the subject are associated with a plurality of groups. Specifically, the memory circuitry 35 stores therein the association information in which the anatomical landmarks of respective sites are associated with the group based on the position in the subject and the sites such as the internal organs, bones, blood vessels, and nerves. FIG. 10A and FIG. 10B are diagrams illustrating examples of the association information according to the first embodiment. For example, as illustrated in FIG. 10A, the memory circuitry 35 stores therein the association information in which the anatomical landmarks are allocated to a group 1 (position), a group 2 (internal organs), a group 3 (bones), a group 4 (blood vessels), and a group 5 (nerves).

As an example, the memory circuitry 35 stores therein the association information in which the "head", "neck", "chest", "abdomen", and "legs" are classified in the group 1 (position). That is, the memory circuitry 35 stores therein, as the group 1 (position), the landmark for identifying the "head", the landmark for identifying the "neck", the landmark for identifying the "chest", the landmark for identifying the "abdomen", and the landmark for identifying the "legs" in association with each other. Similarly, the memory circuitry 35 stores therein the association information in which the "brain", "lung", "heart", "liver" and the like are classified in the group 2 (internal organs). Further, the memory circuitry 35 stores therein the association information in which the "skull bone", "shinbone", "rib bone", "breast bone", "thighbone", and the like are classified in the group 3 (bones). The memory circuitry 35 also stores therein the association information in which the "brain blood vessel", "carotid artery", "main artery", "femoral artery", and the like are classified in the group 4 (blood vessels). Further, the memory circuitry 35 stores therein the association information in which the "optic nerve", "intercostal nerve", "ventral nerve", "femoral nerve", and the like are classified in the group 5 (nerves). That is, the memory circuitry 35 stores therein the landmarks of the respective sites classified in the groups in association with the groups.

The association information is not limited to the above example, and can be stored in various modes. For example, as illustrated in FIG. 10B, the memory circuitry 35 can store therein the association information indicating a hierarchical structure between the groups. For example, the memory circuitry 35 can store therein the association information having the hierarchic structure in which the "chest" in the group 1 is positioned at the top, and the group 2 of the internal organs included in the chest such as the "heart" is arranged beneath thereof. Further, in the association information indicating the hierarchical structure, beneath the "heart" in the group 2, a group 2-1-1 including, for example, "aortal valve", "mitral valve", "pulmonary valve", and "tricuspid valve" and a group 2-1-2 including "right coronary artery" and "left main coronary trunk" are arranged. Further, in the association information indicating the hierarchical structure, beneath the group 2-1-2, a group 2-1-2-1 including, for example, "left anterior descending coronary" and "left circumflex coronary artery" are arranged. In this manner, the memory circuitry 35 can store therein the association information indicating the hierarchical information between the groups.

The association information illustrated in FIG. 10A and FIG. 10B are only examples, and the first embodiment is not limited thereto. That is, the association information stored in the memory circuitry 35 can arbitrarily associate the group and the site with each other. For example, a user can generate the association information in which the group and the site are associated with each other, and can operate to store the association information in the memory circuitry 35.

As described above, in the X-ray CT apparatus 1, the memory circuitry 35 stores the association information therein. The detecting function 37a refers to the association information stored in the memory circuitry 35 to detect the site. The detecting function 37a selects at least one group of the plurality of groups based on the set examination information and the type of scan to be executed, and detects a site of the subject corresponding to the at least one group based on the anatomical landmarks corresponding to the selected group. For example, the detecting function 37a selects a group having a detection granularity corresponding to the examination information and the type of scan. As described above, the association information is divided into groups for each site. The sites in the association information are classified respectively, as illustrated in FIG. 10A, in a large region such as the "head" and "abdomen", and a small region such as the "blood vessels" and "nerves". That is, regarding the sites in the association information, easily detectable sites and hardly detectable sites are associated with different groups in the volume data. In other words, the sites in the association information includes sites that can be detected from the volume data regardless of the conditions such as image quality, and sites that can be hardly detected from the volume data depending on the conditions such as image quality.

The detecting function 37a selects a group based on the examination information and scan conditions, and detects the anatomical landmarks with respect to the landmarks in the site corresponding to the selected group. Specifically, the detecting function 37a acquires the examination information and the scan conditions, and selects a group corresponding to the acquired examination information and scan conditions. The examination information and the scan conditions are acquired from the subject information, a scan plan, and the like. For example, the detecting function 37a acquires the examination information and the scan conditions from the information included in an examination order and information of a scan protocol selected by an operator. As an example, the detecting function 37a acquires "chest to pelvis (liver simple imaging+contrast-enhanced imaging)" as the examination information and the scan conditions.

The examination information and the scan conditions are associated beforehand with the group and stored in the memory circuitry 35. For example, information in which "group 1 (position)", "group 2 (internal organs)", and "group 4 (blood vessels)" are associated with "chest to pelvis (liver simple imaging+contrast-enhanced imaging)" is stored in the memory circuitry 35. The above information can be associated with information related to finer sites in the group. For example, information in which "group 1 (position): chest, abdomen", "group 2 (internal organs): liver", and "group 4 (blood vessels): hepatic artery, hepatic veins" are associated with "chest to pelvis (liver simple imaging+contrast-enhanced imaging)" can be stored in the memory circuitry 35.

The detecting function 37a acquires the examination information and the scan conditions from the subject information, the scan plan, and the like. The detecting function 37a refers to the information indicating the association of the examination information and the scan conditions with the group, thereby acquiring the information of the group corresponding to the acquired examination information and scan conditions. The detecting function 37a then detects the landmarks corresponding to the acquired group by referring to the association information stored in the memory circuitry 35, thereby detecting a site of the subject.

For example, the detecting function 37a acquires "chest to pelvis (liver simple imaging+contrast-enhanced imaging)" as the examination information and the scan conditions. The detecting function 37a then retrieves the information of the group corresponding to the "chest to pelvis (liver simple imaging+contrast-enhanced imaging)" from the memory circuitry 35, and detects landmarks of the site included in the retrieved group from the volume data. For example, when the "group 1 (position)", the "group 2 (internal organs)", and the "group 4 (blood vessels)" are associated with the "chest to pelvis (liver simple imaging+contrast-enhanced imaging)" and when referring to the information illustrated in FIG. 10A, the detecting function 37a detects landmarks classified in the "group 1 (position)", the "group 2 (internal organs)", and the "group 4 (blood vessels)" from the volume data. When the association information has the hierarchical structure as illustrated in FIG. 10B, the detecting function 37a can detect only the landmarks of the "group 2 (internal organs)" and the "group 4 (blood vessels)" positioned beneath the "chest" and the "abdomen" corresponding to the position of the "chest to pelvis", in the "group 1 (position)".

Further, for example, when the "group 1 (position): chest, abdomen", the "group 2 (internal organs): liver", and the "group 4 (blood vessels): hepatic artery, hepatic veins" are associated with the "chest to pelvis (liver simple imaging+ contrast-enhanced imaging)", the detecting function 37a refers to the association information to detect the landmarks for identifying the "chest, abdomen", the landmarks for identifying the "liver", and the landmarks for identifying the "hepatic artery, hepatic veins" from the volume data. In the detection of landmarks described above, detection of the landmarks of the blood vessels is performed with respect to the volume data collected by contrast-enhanced imaging.

As described above, the detecting function 37a selects a group based on the examination information and the scan conditions, and detects the landmarks corresponding to the selected group, thereby detecting a site based on the examination information and the scan conditions from the volume data. For example, the detecting function 37a can detect the site described above with respect to the volume data collected by taking the scanogram image and the volume data collected by the main scan.

As described above, every time the detecting function 37a detects a site from the volume data, the detecting function 37a sequentially stores an identification code in the memory circuitry 35, associated with the coordinate of the landmark corresponding to the detected site. The position matching function 37b retrieves the association information between the coordinate of the landmark and the identification code stored in the memory circuitry 35 to perform the matching processing described above. The position matching function 37b stores a matching result (the coordinate transformation matrix "H") in the memory circuitry 35. For example, the position matching function 37b performs the matching processing every time the detecting function 37a detects a site, and stores a matching result in the memory circuitry 35.

Every time the detecting function 37a detects a site, the display control function 37c controls to output the information indicating the detected site. Specifically, the display control function 37c controls to output the information indicating the detection result obtained by the detecting function 37a to at least one of a display image generated from the volume data and a human model image (a virtual subject image). For example, in at least one of the display image and the virtual subject image, the display control function 37c controls to output an image in which the site detected by the detecting function 37a is more highlighted than other sites.

A case in which a group is selected based on the examination information and the priority of the group for each type of scan is described next. In this case, for example, the detecting function 37a selects a group based on priorities set in advance depending on the examination information and the type of scan. In this case, for example, priorities are given to the group associated with the examination information and the scan conditions. As an example, in the "group 1 (position)", the "group 2 (internal organs)", and the "group 4 (blood vessels)" associated with the "chest to pelvis (liver simple imaging+contrast-enhanced imaging)", "priority: 1" is given to the "group 2 (internal organs)", "priority: 2" is given to the "group 1 (position)", and "priority: 3" is given to the "group 4 (blood vessels)". That is, the detecting function 37a detects landmarks in order of the "group 2 (internal organs)", the "group 1 (position)", and the "group 4 (blood vessels)" from the volume data, when referring to the information described above. As for the groups in the association information having the hierarchical structure, the priorities for detecting the landmarks can be similarly given to the respective groups. Due to this configuration, the X-ray CT apparatus 1 can detect sites according to the priorities set by a user, thereby enabling to detect the sites more efficiently.

The priorities described above can be set arbitrarily by a user. That is, the user can set the priorities for detecting the landmarks appropriately for each of the examination information and the type of scan. The priorities can be sequentially set from a group in which it is desired to detect landmarks preferentially, or can be set in order of easiness of detection. In this case, the X-ray CT apparatus 1 can detect sites efficiently, and can ascertain the detection status of sites based on the anatomical landmarks. As described above, in the conventional detection of sites using the X-ray CT apparatus 1, sites are automatically recognized based on geometric features in the scanogram image and an imaging condition suitable for the recognized site is only set. Detection of sites using the scanogram image does not always work well depending on the image quality and bodily characteristics of the subject. Further, if detection of sites is performed randomly, it may take time to acquire a desired result (detection of an internal organ or the like desired to detect). Therefore, the X-ray CT apparatus 1 according to the first embodiment can ascertain the detection status of a site based on the anatomical landmarks under control of the processing circuitry 37 (the display control function 37c and the control function 37d) described below in detail.

Specifically, in the X-ray CT apparatus 1 according to the first embodiment, the data collection circuitry 14 collects projection data by detecting X rays having penetrated through the subject, and the detecting function 37a detects anatomical landmarks included in the volume data reconstructed from the projection data, thereby detecting sites of the subject. In the X-ray CT apparatus 1, the display control function 37c controls to output the information indicating the detection result obtained by the detecting function 37a. In the X-ray CT apparatus 1 according to the first embodiment, sites are detected in order of priorities set in advance in the subject, and every time a site is detected, the detection result is displayed. That is, the detecting function 37a detects landmarks in order of having the highest priority set beforehand, among the anatomical landmarks included in the volume data, thereby detecting sites of the subject in a stepwise manner. Every time a site is detected, the display control function 37c controls to output the information indicating the detected site.

Figure 11:
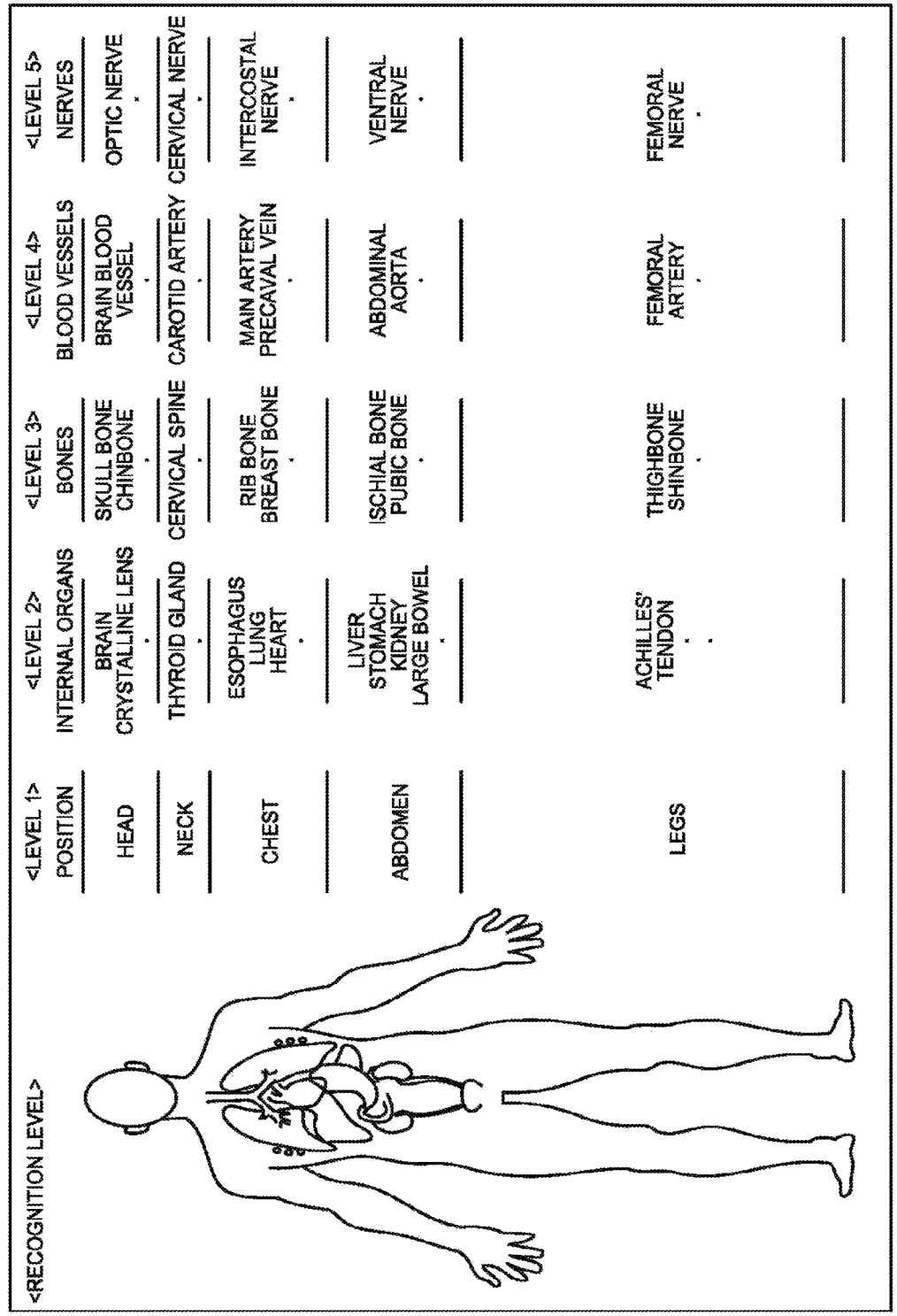
FIG. 11 is an explanatory diagram of an example of priorities of detection sites according to the first embodiment.

The priorities of the sites described above is described here. The priorities in detection of sites can be set arbitrarily. For example, the priorities are set so as to detect a site having a less number of landmarks to be used for detection. That is, priorities are set in such a manner that corresponding landmarks are detected sequentially in a site having a less number of landmarks for detecting a certain region included in the volume data as a site. Accordingly, for example, a site that can be detected more easily is detected more quickly. FIG. 11 is an explanatory diagram of an example of priorities of detection sites according to the first embodiment. In FIG. 11, an example in which priorities are given to the whole body of the subject is illustrated. FIG. 11 illustrates a case where priorities are set to the groups in the association information illustrated in FIGS. 10A and 10B, and easiness of detection is indicated as a recognition level.

For example, the priorities are set, as illustrated in FIG. 11, from a level having high detection priority such as "recognition level: level 1", "recognition level: level 2", "recognition level: level 3", "recognition level: level 4", and "recognition level: level 5". That is, when the detection processing is performed according to the priorities illustrated in FIG. 11, detection is performed from the site of the "recognition level: level 1". The site of the "recognition level: level 1" having the highest priority is, for example, the "position" in the human body, and the "head", "neck", "chest", "abdomen", and "legs" are set thereto. The site of the "recognition level: level 2" having the next highest priority is, for example, the "internal organs" as illustrated in FIG. 11, and "brain" and "crystalline lens" in the "head", "thyroid gland" in the "neck", "esophagus", "lung", and "heart" in the "chest", "liver", "stomach", "kidney", and "large bowel" in the "abdomen", and "Achilles' tendon" in the "legs" are set thereto.

Similarly, "bones" is set as the site having the next priority "recognition level: level 3", and "blood vessels" is set as the next priority "recognition level: level 4", and "nerves" is set as the next priority "recognition level: level 5". The information of the set priorities is stored in the memory circuitry 35, and the detecting function 37a appropriately refers to the information. The example of the recognition level illustrated in FIG. 11 is an example only, and the first embodiment is not limited thereto. For example, such a case can be considered that the priorities in detection of the sites are set according to a scan protocol. That is, when a scan protocol with respect to a predetermined site is selected, the predetermined site is set to be detected with a high priority. As an example, when a scan protocol of tractography with respect to the "nerves" is selected in an MRI apparatus, information in which the "nerves" is set as the site having the "recognition level: level 1" is used. That is, the memory circuitry 35 stores therein the information in which the priorities are set according to the scan protocol. The detecting function 37a retrieves the information of the corresponding priority from the memory circuitry 35 according to the selected scan protocol, and performs the detection processing by referring to the retrieved priority information.

For example, when the priority information illustrated in FIG. 11 is referred to, the detecting function 37a first detects landmarks for detecting the "head", "neck", "chest", "abdomen", and "legs" included in the "position". For example, the detecting function 37a preferentially detects a landmark of the "seventh rib" and a landmark of the "lower end of the lung" for detecting the "chest".

Here, the detecting function 37a detects only the sites at a position included in a range in which the projection data has been collected in imaging of the scanogram image. That is, when the scanogram image has been collected in the range of the "chest" and the "abdomen", the detecting function 37a detects the landmarks for detecting the "chest" and the "abdomen". In other words, when the scanogram image has been collected in the range of the "chest" and the "abdomen", landmarks for detecting the "head", "neck", and "legs" are not detected. In this case, for example, at the time of performing the detection processing, the detecting function 37a first refers to the scan protocol to specify in which site the examination target is, and performs the detection processing.

In this manner, when performing the detection processing for the site of "position", being the "recognition level: level 1" having the highest priority, the detecting function 37a performs the detection processing for the site of the "internal organs", being the "recognition level: level 2". Because having performed detection of the "position" in the former stage, the detecting function 37a can speed up the processing by using the information of the detected "position" to perform the detection processing of the "internal organs". As an example, the detecting function 37a performs processing to detect landmarks of the "internal organs" such as "esophagus", "lung", and "heart" from the region in the volume data corresponding to the position of the "chest" detected in the former stage, in the volume data of the scanogram image. In other words, the detecting function 37a does not perform processing to detect landmarks of the internal organs of the "abdomen" such as "liver", "stomach", "kidney", and "large bowel" from the region in the volume data corresponding to the position of the "chest".

As described above, every time a site is detected from the volume data according to the priorities set in advance, the detecting function 37a sequentially stores the coordinate of the landmark corresponding to the detected site in association with the identification code in the memory circuitry 35. The position matching function 37b retrieves the association information of the coordinate of the landmark with the identification code stored in the memory circuitry 35, and performs the matching processing described above. The position matching function 37b stores the matching results (the coordinate transformation matrix "H") in the memory circuitry 35. For example, the position matching function 37b performs the matching processing every time a site is detected by the detecting function 37a and stores the matching result in the memory circuitry 35.

Every time the detecting function 37a detects a site, the display control function 37c controls to output information indicating the detected site. Specifically, the display control function 37c controls to output the information indicating the detection result obtained by the detecting function 37a to at least one of the display image generated from the three-dimensional image data and the human model image (the virtual subject image). For example, the display control function 37c controls to output an image in which the site detected by the detecting function 37a is more highlighted than other sites, in at least one of the display image and the virtual subject image.

Figure 12A:
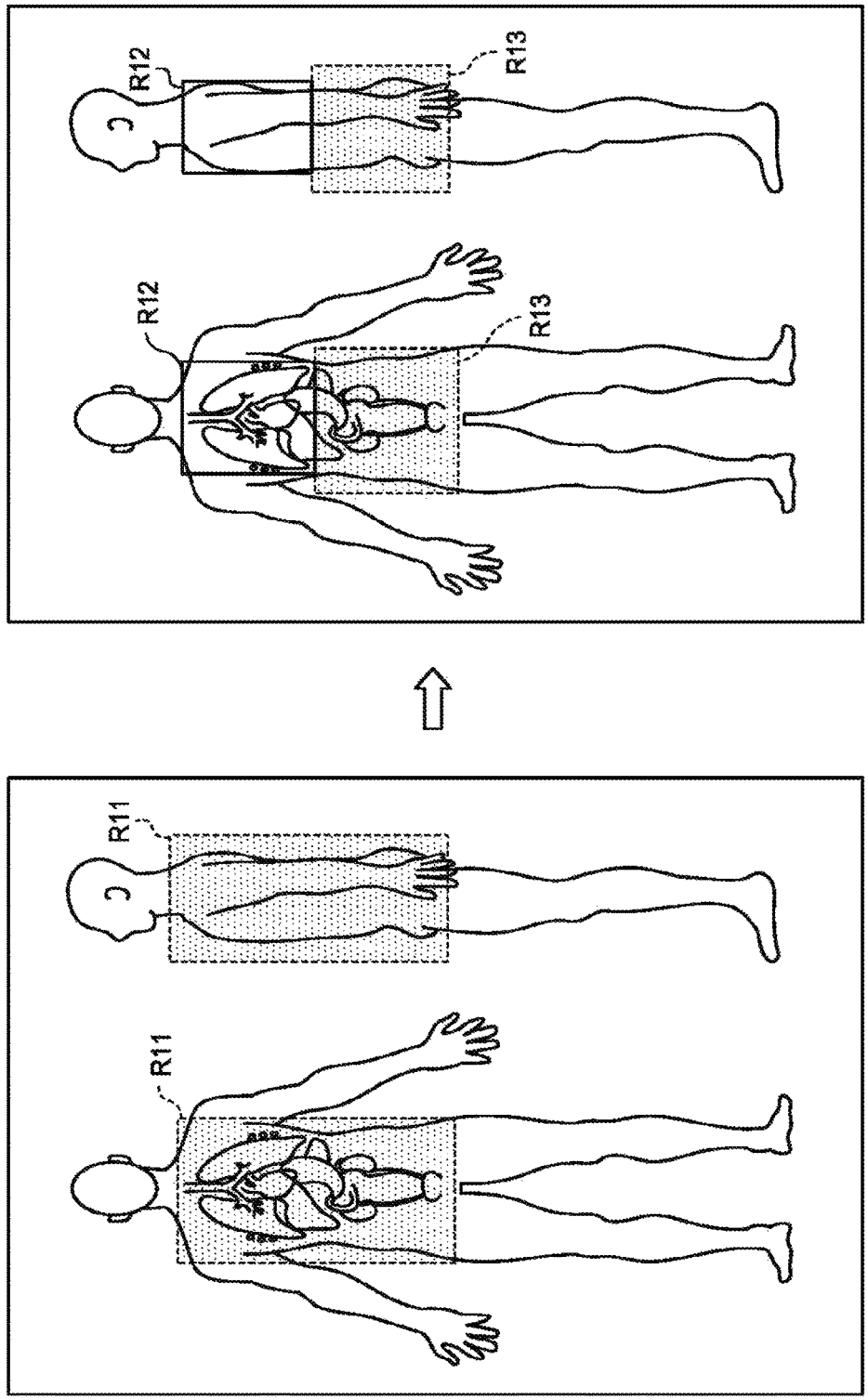
FIG. 12A is a diagram illustrating an example of processing performed with a display control function according to the first embodiment.
Figure 12B:
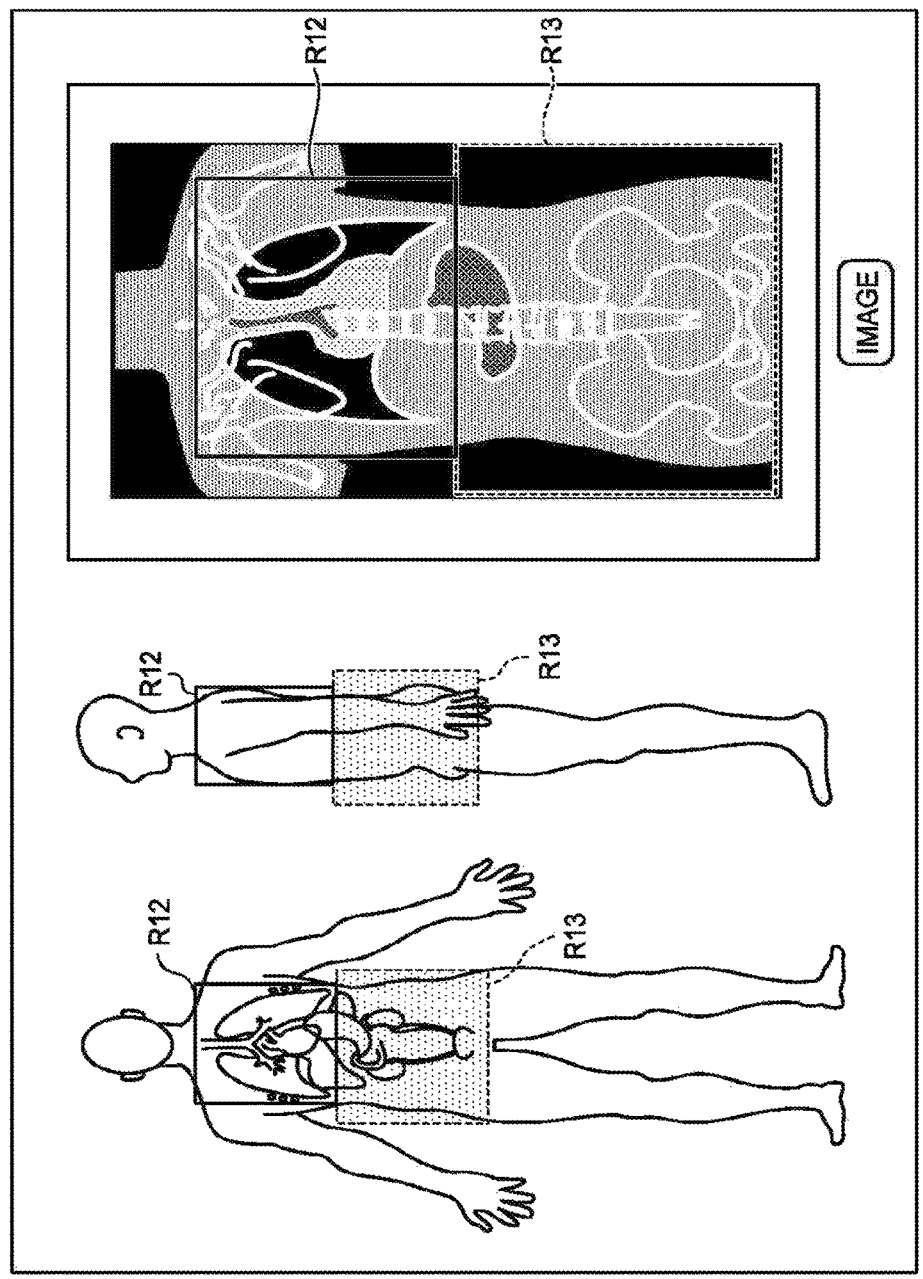
FIG. 12B is a diagram illustrating an example of processing performed with the display control function according to the first embodiment.
Figure 12C:
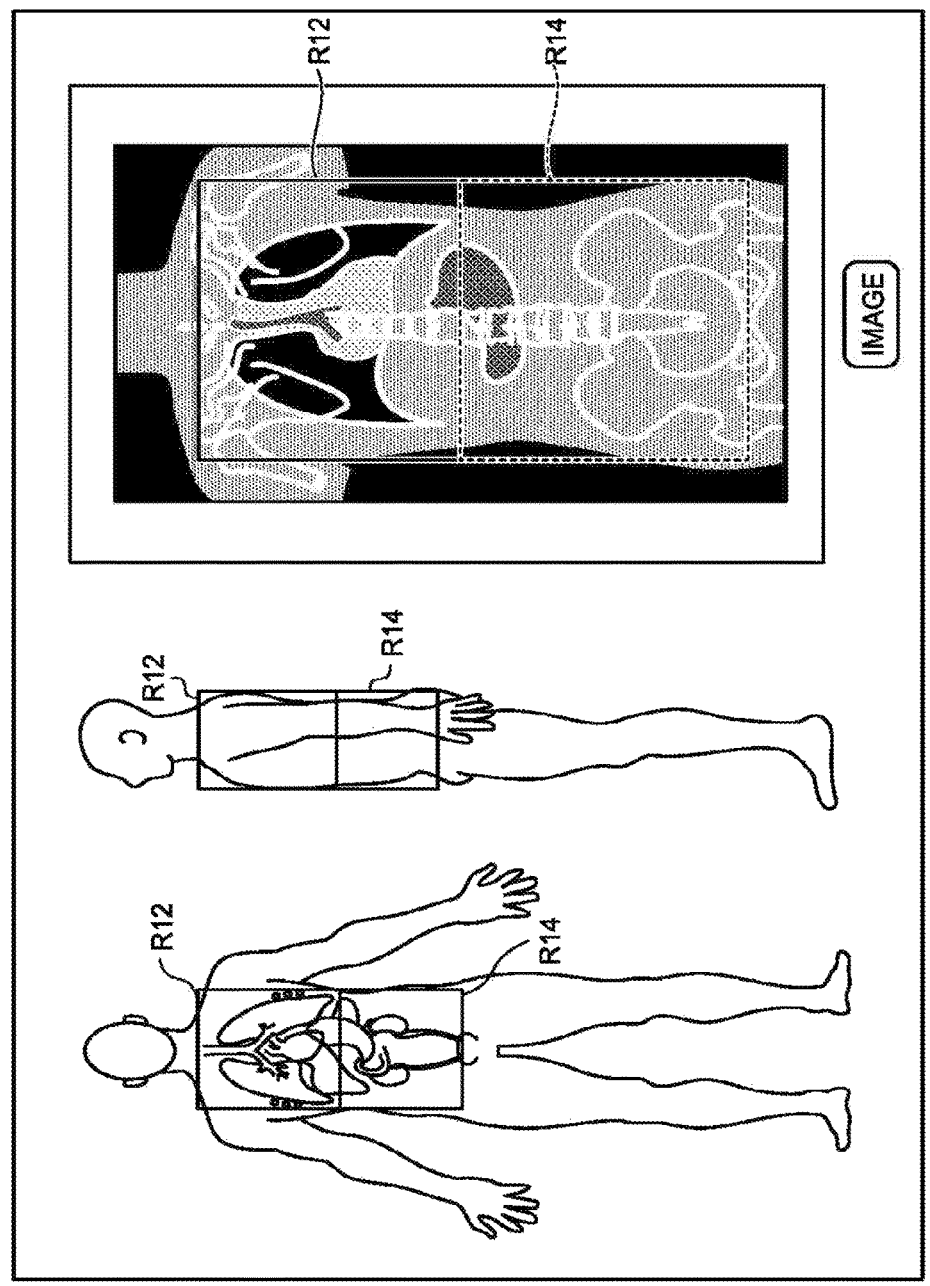
FIG. 12C is a diagram illustrating an example of processing performed with the display control function according to the first embodiment.

FIG. 12A to FIG. 12C are diagrams illustrating examples of the processing performed with the display control function 37c according to the first embodiment. In FIG. 12A to FIG. 12C, a planning screen of the scan plan is illustrated, and a virtual subject image and a scanogram image are illustrated in the planning screen. In FIG. 12A to FIG. 12C, only the virtual subject image or only the virtual subject image and the scanogram image are illustrated. However, in practice, various images to be displayed in the planning screen of the scan image are displayed. For example, when the scanogram images are to be collected, the display control function 37c indicates a scan range R11 of the scanogram image in the virtual subject image, as illustrated in the left diagram in FIG. 12A. This range is a range set in the scan protocol or a range after the scan protocol has been selected and an operator has changed the range. For example, the display control function 37c causes a display to display a virtual subject image in which the scan range R11 of the scanogram image is indicated in gray. When collection of the scanogram images in the scan range R11 indicated on the left side of FIG. 12A, the detecting function 37a performs the detection processing of the landmarks as described above. For example, the detecting function 37a performs the detection processing according to the priorities.

When the "chest" is detected from the volume data of the scanogram images collected in the scan range R11 by the detecting function 37a, and the information of the detected landmarks and the coordinate transformation matrix in the chest calculated by the position matching function 37b are stored in the memory circuitry 35, the display control function 37c retrieves the identification code of the detected landmark, to extract the coordinate of the landmark having the corresponding identification code in the virtual subject image. The display control function 37c applies the coordinate transformation matrix to the extracted coordinate, to calculate a region "R12" of the "chest" on the virtual subject image, and causes the display 32 to display the virtual subject image in which the inside of the calculated region "R12" of the "chest" is clarified as illustrated in the right diagram in FIG. 12A. The display control function 37c causes to display a region "R13" in which a site has not been detected in gray, as illustrated in the right diagram in FIG. 12A.

The display control function 37c can cause to perform display according to the detection result. For example, the display control function 37c can change the color of the detected site or add a mark depending on the detection accuracy of the respective sites detected by the detecting function 37a. As an example, the display control function 37c can perform color coding with respect to the regions according to a difference of the detection accuracy or add a mark indicating the detection accuracy, depending on a rate of the landmarks detected by the detecting function 37a, among all the landmarks included in the site to be detected. For example, it is assumed that there are "50" landmarks for detecting the "chest". The display control function 37c changes the color of the region "R12", depending on the rate of the landmarks detected by the detecting function 37a, of the "50" landmarks. As an example, the display control function 37c changes the color of the region "R12", depending on the respective rates of the landmarks detected by the detecting function 37a, which are "80% or more (40 or more)" "60% or more to less than 80% (30 or more to less than 40)", or "20% or more to less than 60% (10 or more to less than 30)", or "less than 20% (less than 10)".

For example, the memory circuitry 35 stores therein information in which marks or letters indicating the detection accuracy are associated with the respective rates described above. As an example, the memory circuitry 35 stores therein information in which "excellent" is associated with "80% or more (40 or more)", "good" is associated with "60% or more to less than 80% (30 or more to less than 40)", "poor" is associated with "20% or more to less than 60% (10 or more to less than 30)", and "bad" is associated with "less than 20% (less than 10)". The display control function 37c retrieves a letter corresponding to the detection result by the detecting function 37a from the memory circuitry 35, adds the letter to the region "R12", and causes to display the region "R12". In this manner, the display control function 37c changes the color of the detected region or adds a mark thereto depending on the detection accuracy of the respective sites detected by the detecting function 37a. Accordingly, an observer can confirm the detection accuracy of the detected site at a glance.

In this manner, the display control function 37c causes the display 32 to display the virtual subject image in which the site detected by the detecting function 37a is highlighted. The display control function 37c can cause to display the detected site highlighted not only on the virtual subject image but also on the actual scanogram image. In the example described above, a case where a site after the position matching has been performed with the position matching function 37b is displayed in the virtual subject image has been described. However, the embodiment of the present invention is not limited thereto, and the detected site can be highlighted and displayed in the virtual subject image without performing the matching processing. In this case, the display control function 37c can retrieve an identification code stored in the memory circuitry 35, and highlight and display a region defined by the identification code corresponding to the retrieved identification code can on the virtual subject image.

In this manner, the display control function 37c causes to highlight and display the site detected by the detecting function 37a. However, there is no guarantee of success of the detection processing by the detecting function 37a, and there is a case where a site is not detected successfully. Therefore, the display control function 37c can highlight and display a region on the virtual subject image corresponding to the region set on the display image as a site. In this case, the input circuitry 31 receives a designation operation for designating a site of the subject with respect to the display image generated from the three-dimensional image data. The display control function 37c controls to output information indicating the site designated by the designation operation received by the input circuitry 31 is indicated as a detected site.

For example, when an "image" button arranged on the scan planning screen is pressed, the display control function 37c causes to display the collected scanogram image, as illustrated in FIG. 12B, on the scan planning screen on which the virtual subject image is illustrated. As illustrated in FIG. 12B, the display control function 37c causes to display the region "R13" enclosed by a dotted line on a scan image together with the region "R12" in which the sites have been detected on the scanogram image, so as to be distinguished from the detected region "R12". Also in this case, the display control function 37c can change the color of the detected region or add a mark thereto, depending on the detection accuracy of respective sites detected by the detecting function 37a.

An operator can set the site via the input circuitry 31. For example, the operator sets the region of the site by operating the input circuitry 31 to change the size of the region "R13". For example, as illustrated in the right diagram of FIG. 12C, the operator operates the input circuitry 31 to change the region "R13" to a region "R14" for setting the "abdomen". In this manner, when the region "R14" is set, the display control function 37c extracts the coordinates of the landmarks included in the set region. The display control function 37c applies the coordinate transformation matrix to the coordinates of the landmarks in the virtual subject image corresponding to the extracted landmarks, to calculate the region "R14" in the virtual subject image, and displays the virtual subject image in which the calculated region is indicated as "R14". As the coordinate transformation matrix described above, the coordinate transformation matrix calculated in the chest can be used, or the coordinate transformation matrix can be recalculated by using the landmarks included in the region "R14" designated by the operator.

Figure 13:
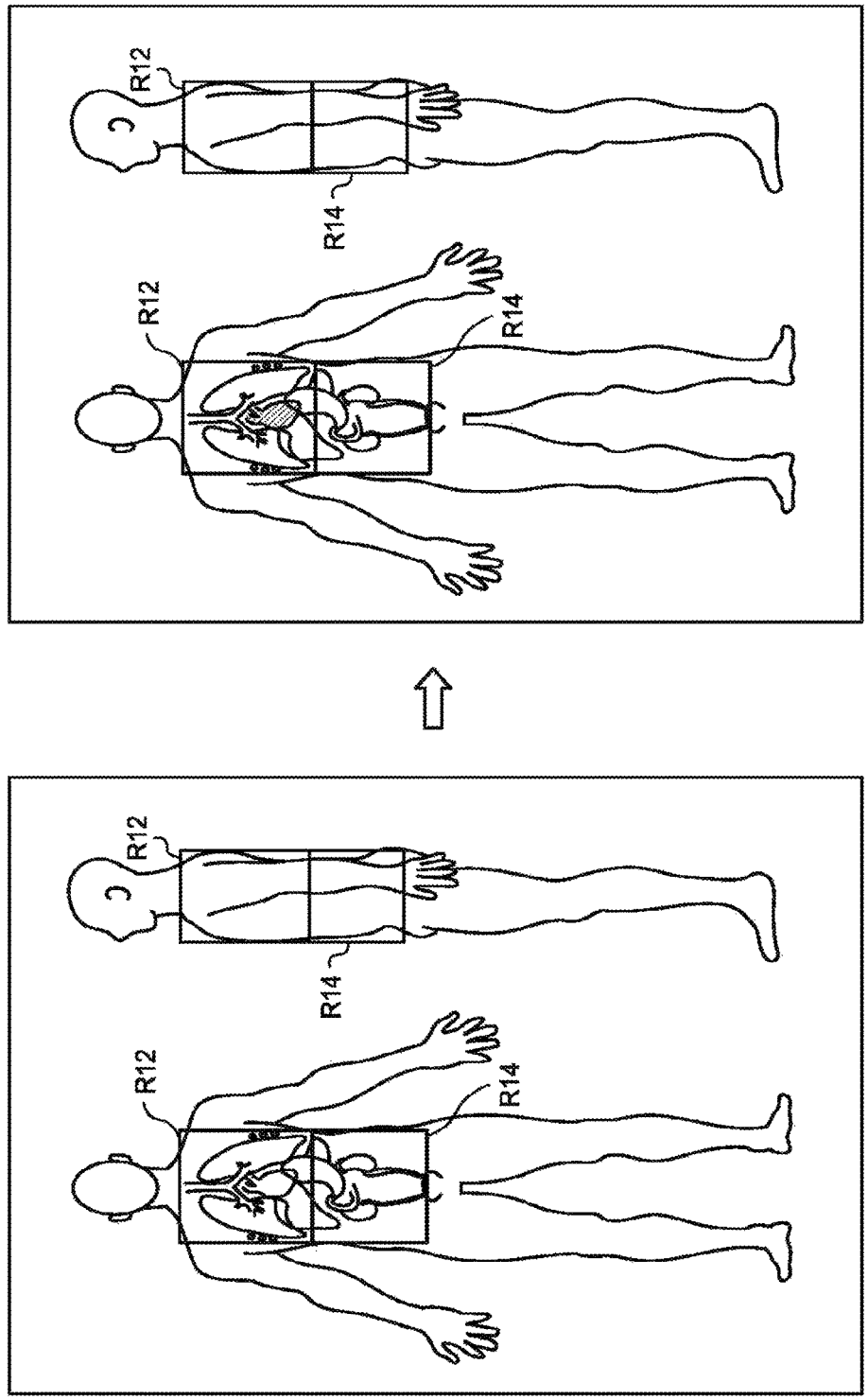
FIG. 13 is a diagram illustrating an example of processing performed with the display control function according to the first embodiment.

When the detecting function 37a detects sites in a stepwise manner, the display control function 37c reflects the pieces of information of the sites in the virtual subject image every time the site is detected. FIG. 13 is a diagram illustrating an example of the processing performed with the display control function 37c according to the first embodiment. For example, as illustrated in the left diagram of FIG. 13, after the chest region "R12" and the abdomen region "R14" have been detected, when the detecting function 37a detects the "heart" from the chest, the display control function 37c causes to display the virtual subject image in which the "heart" is highlighted as illustrated in the right diagram of FIG. 13. Even when the sites are detected in a stepwise manner, the display control function 37c can change the color of the detected region or add a mark thereto depending on the detection accuracy of respective sites detected by the detecting function 37a. For example, the display control function 37c can change the color of the heart region or add a mark or a character to the heart depending on the detection accuracy of the heart.

In this manner, the detecting function 37a detects the sites in a stepwise manner according to the priorities, and the display control function 37c causes to display the virtual subject image or the scanogram image in which the detected site is highlighted, so that an operator can ascertain the detection status of the site based on the anatomical landmarks at a glance. Accordingly, the operator can judge at a glance whether a range desired to scan has been detected by the main scan, and forward the examination.

The detection processing of the site described above can be performed not only with respect to the volume data of the positioning image but also with respect to the volume data collected by the main scan. It is predicted that the images collected by the main scan have higher image quality and higher detection accuracy by the detecting function 37a as compared with the scanogram image. Further, in the main scan, a contrast agent may be used, and thus fine blood vessels and the like can be detected. Therefore, when images are collected by the main scan, the detecting function 37a performs the detection processing according to the priorities described above by using the collected volume data. In the main scan, because the scan is performed by setting the site, for example, the recognition level can be started from the level 2.

Meanwhile, it is also possible to adjust the scan range after the scan range of the main scan is set in advance and the detecting function 37a detects the site. Specifically, the input circuitry 31 receives setting of the scan range for collecting the projection data for diagnosis. The control function 37d adjusts the scan range received by the input circuitry 31 based on the position of the site of the subject detected by the detecting function 37a. That is, the control function 37d controls the scan control circuitry 33 to perform the scan. FIG. 14 is an explanatory diagram of an example of adjustment of the scan range according to the first embodiment.

For example, as illustrated in the top part in FIG. 14, in a state in which the detection processing is being performed with respect to the volume data of the scanogram image and the site has not been detected yet (the inside of the region R11 is in a gray state), an operator sets the scan range of the main scan as the "lung" via the input circuitry 31. In this case, because the lung region in the scanogram image has not been detected yet, an accurate scan range cannot be set. For example, as illustrated in the right diagram on the top part of FIG. 14, the scan range is set in a state with the scan range "R15" of the main scan being deviated from the lung region.

Upon detection of the "lung" in the volume data by the detecting function 37a, the control function 37d sets the scan range "R16" of the main scan accurately including the "lung" as illustrated in the right diagram on the bottom part of FIG. 14, and transmits the set information (the information of the bed position corresponding to the coordinate of the region R16) to the scan control circuitry 33, thereby performing the main scan in the region R16.

The group information described above can be appropriately displayed on the display. For example, the display control function 37c controls the display 32 to display the association information illustrated in FIG. 10A, FIG. 10B, and FIG. 11. That is, the display control function 37c controls the display 32 to display the information indicating the association between the groups and the landmarks included in the respective groups. The group information can be displayed in various modes. As an example, the display control function 37c can display the association information illustrated in FIG. 10A, FIG. 10B, and FIG. 11 on the planning screen of the scan plan. Further, for example, the display control function 37c can display portions corresponding to the group sequentially in the virtual subject image. As an example, the display control function 37c can control to highlight the respective sites from the group 1 to the group 5, while being switched at a fixed time interval. Further, the display control function 37c can control to highlight the sites of a group based on the set scan plan. Accordingly, a user can confirm a site to be detected and can reset a site to be detected by referring to these pieces of information during planning the scan.

Figure 15:
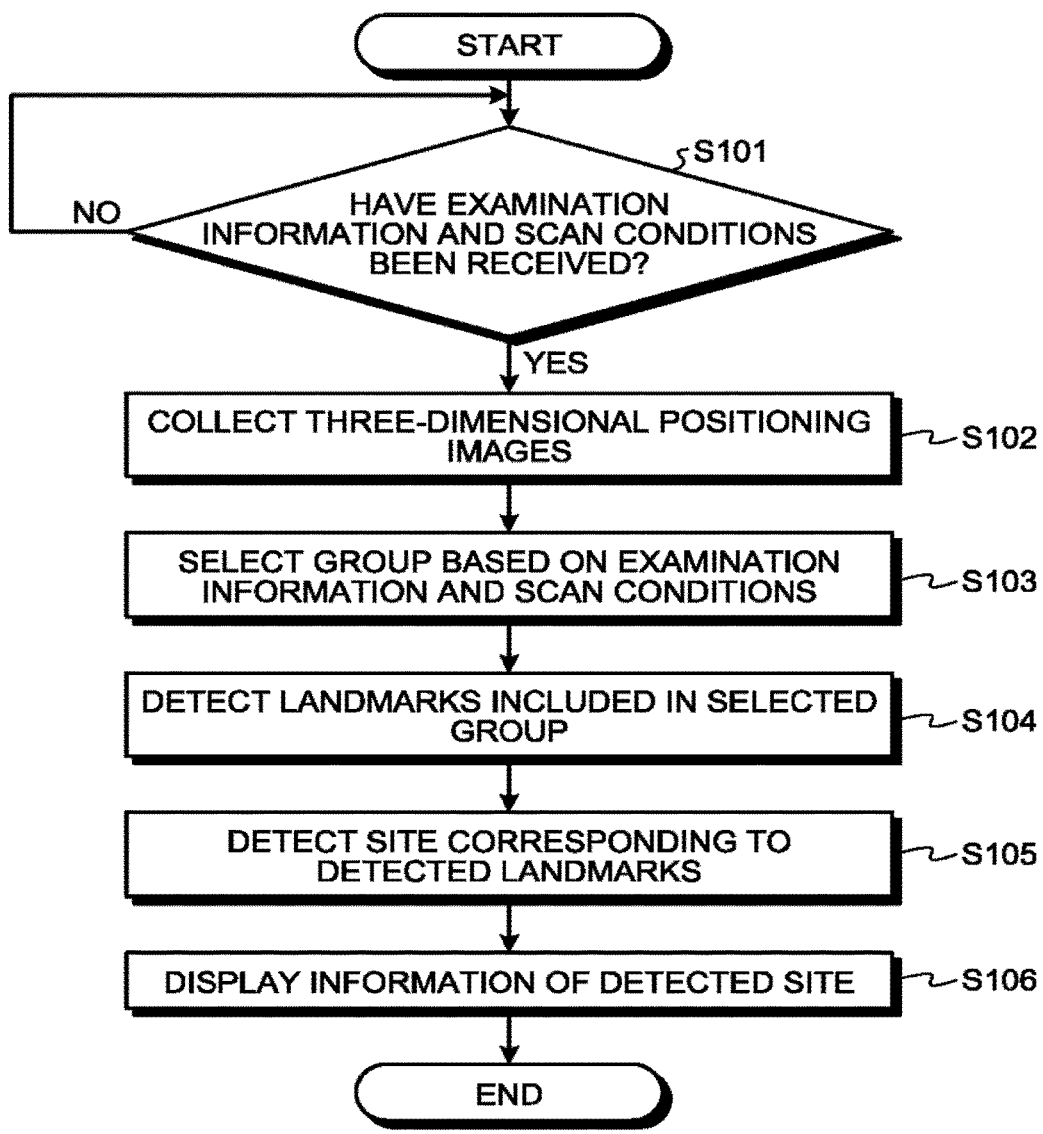
FIG. 15 is a flowchart illustrating a process procedure performed by the X-ray CT apparatus according to the first embodiment.
Figure 16A:
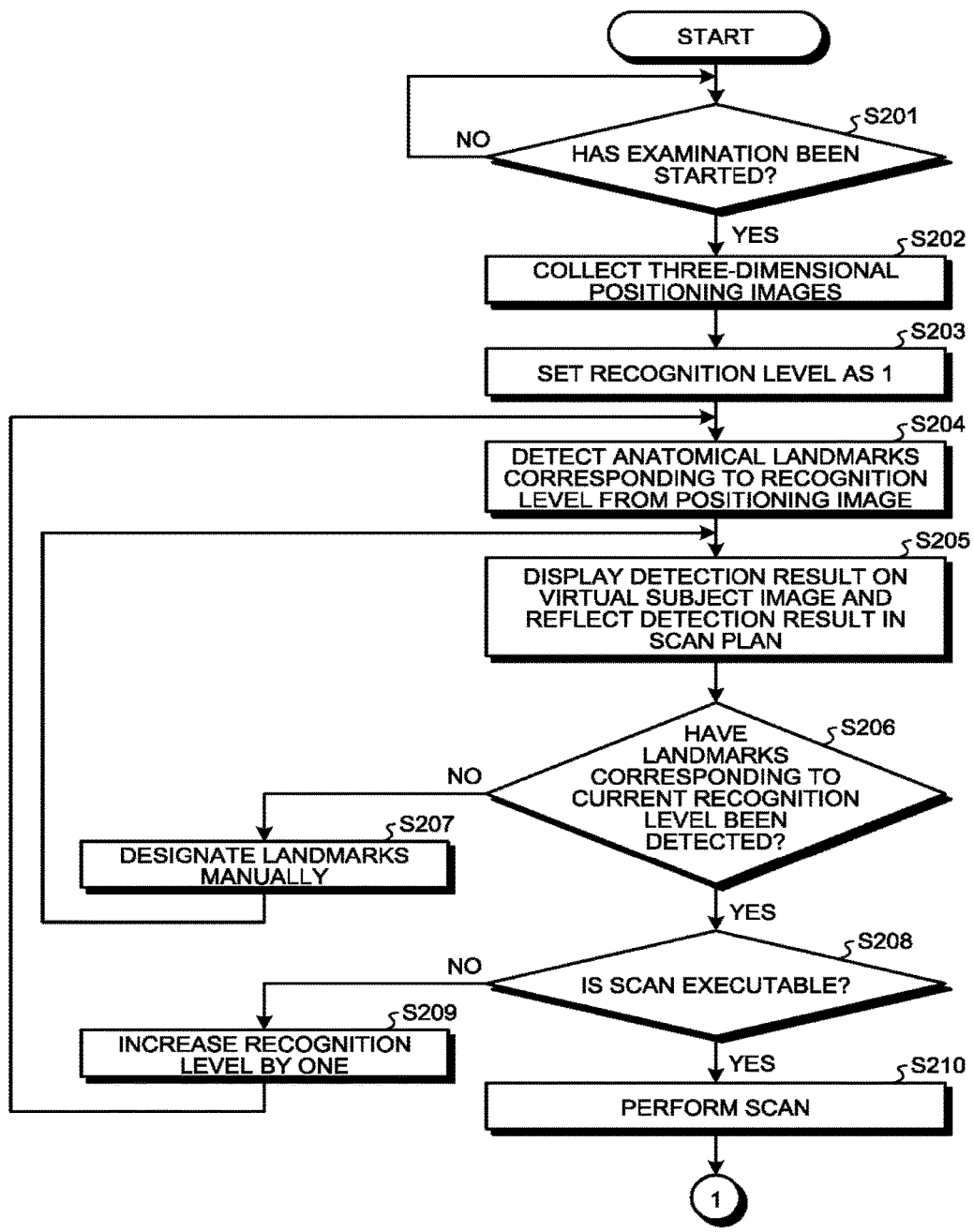
FIG. 16A is a flowchart illustrating a process procedure performed by the X-ray CT apparatus according to the first embodiment.
Figure 16B:
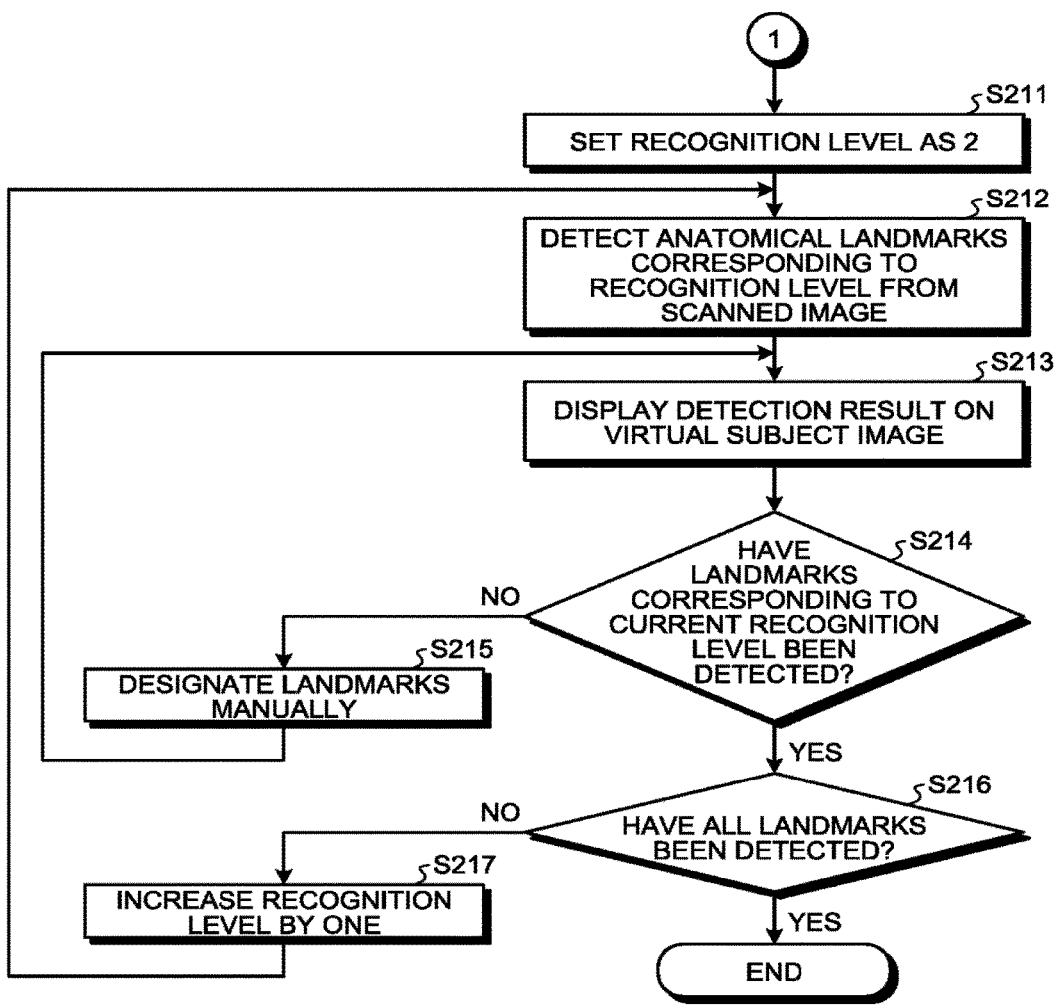
FIG. 16B is a flowchart illustrating a process procedure performed by the X-ray CT apparatus according to the first embodiment.

The processing performed by the X-ray CT apparatus 1 according to the first embodiment is described next with reference to FIG. 15, FIG. 16A, and FIG. 16B. FIG. 15, FIG. 16A, and FIG. 16B are flowcharts illustrating process procedures performed by the X-ray CT apparatus 1 according to the first embodiment. FIG. 15 illustrates an example of a process of selecting a group based on examination information and scan conditions to detect a site. FIGS. 16A and 16B illustrate an example of a process of detecting a site based on the priorities.

Steps S101 and S102 illustrated in FIG. 15 are steps at which the processing circuitry 37 retrieves the program corresponding to the control function 37d from the memory circuitry 35 and executes the program. At Step S101, the processing circuitry 37 determines whether the examination information and the scan conditions have been received. At Step S102, the processing circuitry 37 controls the scan control circuitry 33, the image reconstruction circuitry 36, and the like to collect the three-dimensional positioning images.

Steps S103 to S105 illustrated in FIG. 15 are steps at which the processing circuitry 37 retrieves the program corresponding to the detecting function 37a from the memory circuitry 35 and executes the program. At Step S103, the processing circuitry 37 selects a group based on the examination information and the scan conditions. At Step S104, the processing circuitry 37 detects landmarks included in the selected group from the volume data. At Step S105, the processing circuitry 37 detects a site corresponding to the detected landmarks.

Step S106 illustrated in FIG. 15 is a step at which the processing circuitry 37 retrieves the program corresponding to the display control function 37c from the memory circuitry 35 and executes the program. At Step S106, the processing circuitry 37 causes the display 32 to display information of the detected site.

Step S201 and Step S202 illustrated in FIG. 16A are steps at which the processing circuitry 37 retrieves the program corresponding to the control function 37d from the memory circuitry 35 and executes the program. At Step S201, the processing circuitry 37 determines whether the examination has been started. At Step S202, the processing circuitry 37 controls the scan control circuitry 33, the image reconstruction circuitry 36, and the like to collect the three-dimensional positioning images.

Step S203 and Step S204 in FIG. 16A are steps at which the processing circuitry 37 retrieves the program corresponding to the detecting function 37a from the memory circuitry 35 and executes the program. At Step S203, the processing circuitry 37 sets a recognition level in the detection processing to 1. At Step S204, the processing circuitry 37 detects anatomical landmarks corresponding to the recognition level from the positioning image.

Step S205 in FIG. 16A is a step at which the processing circuitry 37 retrieves the program corresponding to the display control function 37c from the memory circuitry 35 and executes the program. At Step S205, the processing circuitry 37 displays the detection result on the virtual subject image, and reflects the detection result in the scan plan.

Step S206 illustrated in FIG. 16A is a step at which the processing circuitry 37 retrieves the program corresponding to the detecting function 37a from the memory circuitry 35 and executes the program. At Step S206, the processing circuitry 37 determines whether the landmarks corresponding to the current recognition level have been detected. Step S207 illustrated in FIG. 16A is a step performed by the input circuitry 31. At Step S207, when it is determined that the landmarks corresponding to the current recognition level have not been detected (NO at Step S206), the input circuitry 31 receives manual designation.

Step S208 and Step S210 illustrated in FIG. 16A are steps at which the processing circuitry 37 retrieves the program corresponding to the control function 37d from the memory circuitry 35 and executes the program. At Step S208, the processing circuitry 37 determines whether scan is executable. At Step S210, when it is determined that the scan is executable (YES at Step S208), the processing circuitry 37 performs the main scan.

Step S209 illustrated in FIG. 16A is a step at which the processing circuitry 37 retrieves the program corresponding to the detecting function 37a from the memory circuitry 35 and executes the program. At Step 3209, when it is determined that the scan is not executable (NO at Step S208), the processing circuitry 37 increases the recognition level in the detection processing by 1, and returns to Step S204 to detect the anatomical landmarks corresponding to the recognition level.

Step S211 and Step S212 illustrated in FIG. 16B are steps after the main scan at Step S210 has been performed, and the processing circuitry 37 retrieves the program corresponding to the detecting function 37a from the memory circuitry 35 and executes the program. At Step S211, the processing circuitry 37 sets the recognition level in the detection processing to 2. At Step S212, the processing circuitry 37 detects the anatomical landmarks corresponding to the recognition level from the scanned image.

Step S213 illustrated in FIG. 16B is a step at which the processing circuitry 37 retrieves the program corresponding to the display control function 37c from the memory circuitry 35 and executes the program. At Step S213, the processing circuitry 37 displays the detection result on the virtual subject image. Step S214 illustrated in FIG. 16B is a step at which the processing circuitry 37 retrieves the program corresponding to the detecting function 37a from the memory circuitry 35 and executes the program. At Step S214, the processing circuitry 37 determines whether the landmarks corresponding to the current recognition level have been detected. Step S215 illustrated in FIG. 16B is performed by the input circuitry 31. At Step S215, when it is determined that the landmarks corresponding to the current recognition level have not been detected (NO at Step S214), the input circuitry 31 receives manual designation.

Step S216 illustrated in FIG. 16B is a step at which the processing circuitry 37 retrieves the program corresponding to the control function 37d from the memory circuitry 35 and executes the program. At Step S216, the processing circuitry 37 determines whether all the landmarks have been detected. When it is determined that all the landmarks have been detected (YES at Step S216), the X-ray CT apparatus 1 finishes the process.

Step S217 illustrated in FIG. 16B is a step at which the processing circuitry 37 retrieves the program corresponding to the detecting function 37a from the memory circuitry 35 and executes the program. At Step S217, when it is determined that all the landmarks have not been detected (NO at Step S216), the processing circuitry 37 increases the recognition level in the detection processing by 1, and returns to Step S212 to detect the anatomical landmarks corresponding to the recognition level from the scanned image.

As described above, according to the first embodiment, the image reconstruction circuitry 36 generates a three-dimensional image data of the subject. The memory circuitry 35 stores therein a plurality of anatomical landmarks in the subject in association with the plurality of groups. The detecting function 37a selects at least one group among the groups based on the set examination information and the type of scan to be performed, and detects a corresponding site of the subject corresponding to the at least one group, based on the anatomical landmarks corresponding to the selected group. The display control function 37c control to output the information indicating the detected site. Therefore, the X-ray CT apparatus 1 according to the first embodiment can detect the site according to the examination status, and detect the site efficiently.

According to the first embodiment, the detecting function 37a selects a group having a detection granularity corresponding to the examination information and the type of scan. Therefore, the X-ray CT apparatus 1 according to the first embodiment can perform the detection processing depending on the state of the collected volume data, and can detect the site efficiently.

According to the first embodiment, the data collection circuitry 14 collects the projection data by detecting X rays having penetrated through the subject. The detecting function 37a sequentially detects landmarks from the one having the highest priority set beforehand, among the anatomical landmarks included in the three-dimensional image data reconstructed from the projection data, thereby detecting the sites of the subject in a stepwise manner. The display control function 37c controls to output the information indicating the detected site, every time the detecting function 37a detects the site. Therefore, the X-ray CT apparatus 1 according to the first embodiment enables to ascertain the detection status of the site based on the anatomical landmarks.

According to the first embodiment, the priorities are set so that sites are detected sequentially from a site having a less number of landmarks to be used for detection. Accordingly, the X-ray CT apparatus 1 according to the first embodiment enables to improve the detection efficiency.

According to the first embodiment, the display control function 37c controls to output the information indicating the detection result obtained by the detecting function 37a to at least one of the display image generated from the three-dimensional image data and the human model image (the virtual subject image). Further, the display control function 37c controls to output an image in which the site detected by the detecting function 37a is more highlighted than other sites, in at least one of the display image and the human model image (the virtual subject image). Therefore, the X-ray CT apparatus 1 according to the first embodiment enables to ascertain the detection status more easily.

According to the first embodiment, the input circuitry 31 receives the designation operation for designating a site of the subject with respect to the display image generated from the three-dimensional image data. The display control function 37c controls to output the information indicating the site designated by the designation operation received by the input circuitry 31 is indicated as a detected site. Therefore, the X-ray CT apparatus 1 according to the first embodiment can easily correspond to a case where the detection processing has not been performed successfully.

According to the first embodiment, the input circuitry 31 receives setting of the scan range for collecting the projection data for diagnosis. The control function 37d adjusts the scan range received by the input circuitry 31 based on the position of the site of the subject detected by the detecting function 37a. Therefore, the X-ray CT apparatus 1 according to the first embodiment enables to perform accurate setting of the scan range without waiting for the detection processing.

Second Embodiment

In the first embodiment described above, a case where sites are detected from volume data according to the priorities set in advance has been described. In a second embodiment, processing in a case where a detection result detected from volume data is different from a standard body type is described. In the second embodiment, the processing contents of the detecting function 37a and the display control function 37c are different from those of the first embodiment. These different points are mainly described below.

The display control function 37c according to the second embodiment controls to output at least one type of information, among information of a site different from the standard form of the site of the subject detected by the detecting function 37a and information of a foreign body included in the subject. FIG. 17 is a diagram illustrating an example of the processing performed with the display control function according to the second embodiment. For example, if the detecting function 37a detects only the landmarks corresponding to the right lung and does not detect the landmarks corresponding to the left lung, when performing the detection processing of the "lung", the detecting function 37a does not indicate that the "lung" is not detected, but directly stores the detection result in the memory circuitry 35.

That is, the detecting function 37a stores the coordinates of the landmarks of the right lung in which the landmarks have been detected and the identification codes in association with each other in the memory circuitry 35. Upon retrieval of the information described above from the memory circuitry 35, the display control function 37c causes the display 32 to display the information reflecting the detection result described above. For example, the display control function 37c causes to display the virtual subject image in which only the right lung is highlighted, as illustrated in the left diagram in FIG. 17. Accordingly, it can be presented to an operator that the body type of the subject is different from the standard type. That is, by presenting the virtual subject image on the left side of FIG. 17 to the operator, the operator can be urged to check the actual scanogram image. Accordingly, the operator can check the actual scanogram image illustrated in the right diagram of FIG. 17 to recognize that the subject has only one lung, and write it in a record.

If the detected site is enlarged as compared with a standard site, the display control function 37c can cause to display information notifying this matter. For example, if the internal organ is enlarged abnormally, is small, or meanders, the display control function 37c presents the information thereof to the operator. For example, when the display control function 37c determines whether the heart is enlarged by comparing the size of the heart detected by the detecting function 73a with the standard size of the heart, and determines that the heart is enlarged, the display control function 37c causes the display to display this information. The display control function 37c determines here whether a cardiothoracic ratio exceeds 50% as the determination of enlargement of the heart, and if the cardiothoracic ratio exceeds 50%, the display control function 37c presents the display information as heart enlargement.

Figure 18:
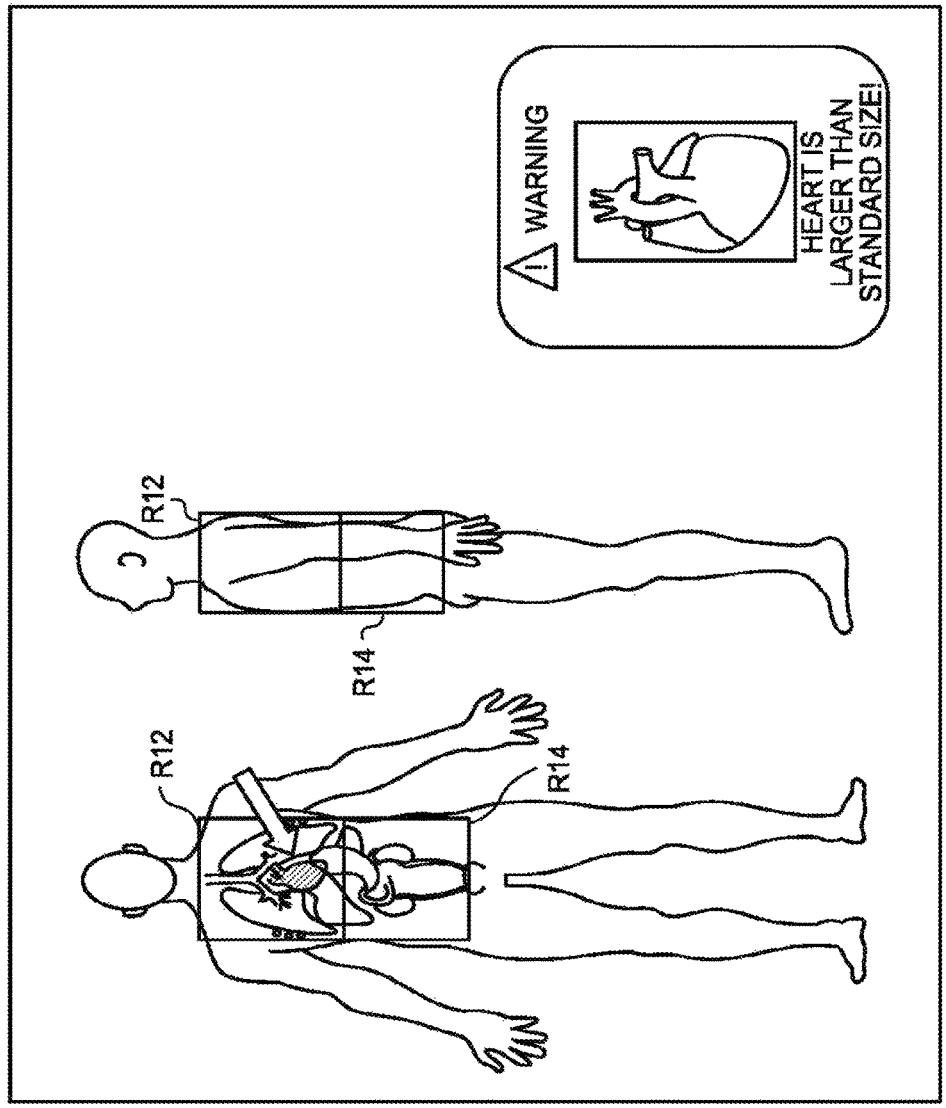
FIG. 18 is a diagram illustrating an example of processing performed with the display control function according to the second embodiment.

FIG. 18 is a diagram illustrating an example of processing performed with the display control function 37c according to the second embodiment. For example, as illustrated in FIG. 18, the display control function 37c adds an arrow to the heart, adds coloring, activates the light in animation, or issues a warning to present the information of heart enlargement to an operator.

The display control function 37c can control to output evaluation information with respect to the site of the subject detected by the detecting function 37a. For example, when the detected site is the heart, the display control function 37c displays the evaluation information based on a calcium score for performing quantitative evaluation of calcification of the coronary artery. In this case, the control function 37d calculates the calcium score based on a CT value. The display control function 37c causes to display the evaluation information based on the calcium score calculated by the control function 37d. As an example, when the calcium score exceeds "600", the display control function 37c causes to display a warning with respect to execution of the CT heart scan (coronary CT). Accordingly, an observer can judge that the CT heart scan is not appropriate as the examination with respect to the target subject.

As described above, the display control function 37c compares the detected internal organ with the standard internal organ, and when the detected internal organ is largely different from the standard, the display control function 37c presents the information. Further, the display control function 37c controls to output the evaluation information with respect to the site of the subject detected by the detecting function 37a. As such information, not only the information related to the internal organs but also similar information can be presented, for example, if there is metal or foreign body in the body. For example, metal and the like can be detected by the CT value. For example, if a CT value different from a human CT value is detected, the display control function 37c presents information related to such a warning described above.

The control function 37d registers information different from the standard as described above in an HIS or an RIS. Accordingly, when the same subject has an examination next time, the information can be retrieved and used. For example, when there is the one-lung information in the subject's information, the detecting function 37a can acquire the one-lung information beforehand and can use the information for the detection processing.

Such pieces of information can be used also as the learning information. For example, when only one lung has been detected and an operator checks the image and registers that the subject has only one lung, the detecting function 37a can learn the way of detection of landmarks and the one-lung information. In this manner, the detecting function 37a learns the association between the site different from the standard form and the landmarks corresponding to the different site, of the sites of the subject, and detects the sites of the subject based on the learning result.

Further, learning by the detecting function 37a can be performed for not only the association between a site and a landmark, but also for metal or the like. For example, by learning information of metal to be used in a surgery and how to detect the metal, the metal present in a subject body can be specified in the stage of detection processing with respect to volume data.

Third Embodiment

While the first embodiment has been described above, the present invention can be also carried out in various other embodiments other than the first embodiment described above.

In the first and second embodiments described above, an embodiment at the time of detecting a site has been described. The X-ray CT apparatus 1 according to a third embodiment can control scan conditions and image reconstruction based on information of a detected site.

For example, if metal is contained in a subject body, or if the body type of the subject has sharply changed locally, noise is included in data to be collected. If the detection processing is not performed well due to the noise, the detecting function 37a causes the image reconstruction circuitry 36 to reconstruct the volume data so as to remove the noise from projection data, and performs the detection processing by using the newly reconstructed volume data. For example, the image reconstruction circuitry 36 uses the original projection data of the volume data in which the detection processing has not been performed well due to the noise to perform image reconstruction again by successive approximation reconstruction, thereby reconstructing new volume data. The detecting function 37a detects the sites of the subject included in the volume data newly reconstructed.

For example, the scan conditions can be controlled based on the detection result obtained by the detecting function 37a. As an example, when the subject has only one lung, the control function 37d executes control to move a bed so that one lung is in the imaging center and control the collimator 12c and the wedge 12b so as to be able to collect one-lung images. For example, the control function 37d modulates the tube current to decrease the radiation dose at a rotation angle at which the one lung to be imaged is away from the focal point of X rays, as compared with other angles. Further, for example, if pleural effusion accumulates in the lung, the control function 37d controls to increase the radiation dose to collect the images.

While the X-ray CT apparatus according to the embodiments above performs the various types of processing, the embodiments are not limited thereto. Alternatively, other medical image diagnostic apparatus may perform the various types of processing, for example. In this case, the medical image diagnostic apparatus, such as an X-ray diagnostic apparatus, an MRI apparatus, and an ultrasonic diagnostic apparatus, includes processing circuitry similar to the processing circuitry 37 and performs the processing described above using acquired medical image data.

Respective constituent elements of the respective devices described in the first embodiment are functionally conceptual, and physically the same configuration as illustrated in the drawings is not always necessary. That is, specific modes of distribution and integration of the respective devices are not limited to those illustrated in the drawings, and a part of all thereof can be functionally or physically distributed or integrated in an arbitrary unit, according to various types of loads and status of use. Further, an arbitrary part of all of processing functions executed in the respective units can be realized by a CPU and a program analyzed and executed in the CPU, or realized as hardware by a wired logic.

The control method described in the first embodiment can be realized by executing a control program prepared in advance on a computer such as a personal computer or a workstation. The control program can be distributed via a network such as the Internet. Further, the control program can be executed by recording it in a computer-readable recording medium such as a hard disk, a flexible disk (FD), a CD-ROM, an MO, and a DVD, and reading it from the recording medium by a computer.

As described above, according to the respective embodiments, it is possible to ascertain the detection status of a site based on anatomical landmarks.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
memory circuitry to store therein a set of anatomical landmarks in a subject for each of a plurality of groups being different in detection granularity, the plurality of groups corresponding to at least two of position, organ, bone, blood vessel, and nerve of the subject; and
processing circuitry configured to
generate three-dimensional image data of the subject,
select one group of the plurality of groups based on set examination information and a type of scan to be performed,
detect, in the three-dimensional image data, a first target site, based on a first set of the anatomical landmarks corresponding to the first target site having been classified into the selected group,
detect, after detection of the first target site, in the three-dimensional image data, a second target site, based on a second set of the anatomical landmarks corresponding to the second target site having been classified into the selected group, and
output information indicating the detected first target site and the detected second target site,
wherein a number of the anatomical landmarks corresponding to the first target site is lower than a number of the anatomical landmarks corresponding to the second target site.

2. The medical image diagnostic apparatus according to claim 1, wherein the processing circuitry is further configured to select the group based on the detection granularity according to the examination information and the type of scan.

3. The medical image diagnostic apparatus according to claim 1, wherein the processing circuitry is further configured to select the group based on priorities set in advance according to the examination information and the type of scan.

4. The medical image diagnostic apparatus according to claim 1, wherein the processing circuitry is further configured to output information indicating a detection result of the first target site and the second target site to at least one of a display image generated from the three-dimensional image data and a human model image.

5. The medical image diagnostic apparatus according to claim 4, wherein the processing circuitry is further configured to output an image in which the detected first target site and the detected second target site are more highlighted than other sites, in at least one of the display image and the human model image.

6. The medical image diagnostic apparatus according to claim 1, wherein the processing circuitry is further configured to
receive a designation operation for designating a site of the subject with respect to a display image generated from the three-dimensional image data, and
output information indicating a site designated by the received designation operation as a detected target site.

7. The medical image diagnostic apparatus according to claim 1, wherein the processing circuitry is further configured to
receive a setting of a scan range for collecting pieces of projection data for diagnosis, and
adjust a received scan range based on a position of the detected first target site and a position of the detected second target site.

8. The medical image diagnostic apparatus according to claim 1, further comprising reconstruction circuitry configured to reconstruct the three-dimensional image data so as to remove noise from collected pieces of projection data, wherein
the processing circuitry is further configured to detect the first target site and the second target site included in three-dimensional image data reconstructed by the reconstruction circuitry.

9. The medical image diagnostic apparatus according to claim 8, wherein the reconstruction circuitry is further configured to reconstruct the three-dimensional image data so as to remove metal contained in the subject and noise, based on a body type of the subject.

10. The medical image diagnostic apparatus according to claim 1, wherein the processing circuitry is further configured to control scan conditions for collecting pieces of projection data for diagnosis based on a position of the detected first target site and a position of the detected second target site.

11. The medical image diagnostic apparatus according to claim 10, wherein the processing circuitry is further configured to control at least one of an irradiation condition of X rays, an irradiation range, and a bed position at a time of collecting the pieces of projection data for diagnosis, based on the position of the detected first target site and the position of the detected second target site.

12. The medical image diagnostic apparatus according to claim 1, wherein the processing circuitry is further configured to control to output at least one piece of information, among information of a site different from a standard form of the detected first target site and the detected second target site and information of a foreign body contained in the subject.

13. The medical image diagnostic apparatus according to claim 1, wherein the processing circuitry is further configured to learn an association between a site different from a standard form of the sites of the subject and a landmark corresponding to the different site, and detect the first target site and the second target site based on a learning result.

14. The medical image diagnostic apparatus according to claim 1, wherein the processing circuitry is further configured to output information related to the plurality of groups.

\* \* \* \* \*